(12) United States Patent
Smolke et al.

(10) Patent No.: US 10,240,175 B2
(45) Date of Patent: *Mar. 26, 2019

(54) COMPOSITIONS AND METHODS FOR PRODUCING BENZYLISOQUINOLINE ALKALOIDS

(71) Applicant: California Institute of Technology, Pasadena, CA (US)

(72) Inventors: Christina D. Smolke, Menlo Park, CA (US); Kristy M. Hawkins, Oakland, CA (US)

(73) Assignee: California Institute of Technology, Pasadena, CA (US)

(*) Notice: Subject to any disclaimer, the term of this patent is extended or adjusted under 35 U.S.C. 154(b) by 21 days.

This patent is subject to a terminal disclaimer.

(21) Appl. No.: 15/078,874

(22) Filed: Mar. 23, 2016

(65) Prior Publication Data

US 2016/0304923 A1  Oct. 20, 2016

Related U.S. Application Data

(60) Continuation of application No. 14/614,484, filed on Feb. 5, 2015, now Pat. No. 9,322,039, which is a
(Continued)

(51) Int. Cl.
*C12P 17/12* (2006.01)
*C12N 1/20* (2006.01)
(Continued)

(52) U.S. Cl.
CPC ............ *C12P 17/12* (2013.01); *C12N 9/0022* (2013.01); *C12N 9/0059* (2013.01);
(Continued)

(58) Field of Classification Search
None
See application file for complete search history.

(56) References Cited

U.S. PATENT DOCUMENTS 7,037,674 B1  5/2006  Kutchan et al.
7,045,290 B2  5/2006  Lindquist et al.
(Continued)

FOREIGN PATENT DOCUMENTS

EP  1512748 A1  3/2005
EP  1837396 A1  9/2007
(Continued)

OTHER PUBLICATIONS

Co-pending U.S. Appl. No. 15/360,763, filed Nov. 23, 2013.
(Continued)

*Primary Examiner* — Yong D Pak
(74) *Attorney, Agent, or Firm* — Wilson Sonsini Goodrich & Rosati

(57) ABSTRACT

The present invention relates to host cells that produce compounds that are characterized as benzylisoquinolines, as well as select precursors and intermediates thereof. The host cells comprise one, two or more heterologous coding sequences wherein each of the heterologous coding sequences encodes an enzyme involved in the metabolic pathway of a benzylisoquinoline, or its precursors or intermediates from a starting compound. The invention also relates to methods of producing the benzylisoquinoline, as well as select precursors and intermediates thereof by culturing the host cells under culture conditions that promote expression of the enzymes that produce the benzylisoquinoline or precursors or intermediates thereof.

19 Claims, 30 Drawing Sheets

Specification includes a Sequence Listing.

Engineered BIA pathway
(up to (S)-reticuline synthesis)   Figure 1

Related U.S. Application Data division of application No. 11/875,814, filed on Oct. 19, 2007, now Pat. No. 8,975,063.

(60) Provisional application No. 60/859,149, filed on Nov. 15, 2006, provisional application No. 60/852,954, filed on Oct. 19, 2006.

(51) Int. Cl.
| | |
|---|---|
| C12N 9/00 | (2006.01) |
| C12N 15/00 | (2006.01) |
| C12N 9/02 | (2006.01) |
| C12N 9/14 | (2006.01) |
| C07H 21/04 | (2006.01) |
| C12N 9/88 | (2006.01) |
| C12N 9/10 | (2006.01) |
| C12N 15/81 | (2006.01) |
| C12N 9/06 | (2006.01) |
| C12P 7/24 | (2006.01) |
| C12P 13/00 | (2006.01) |
| C12P 17/18 | (2006.01) |

(52) U.S. Cl.
CPC ......... *C12N 9/1007* (2013.01); *C12N 9/1096* (2013.01); *C12N 9/88* (2013.01); *C12N 15/81* (2013.01); *C12P 7/24* (2013.01); *C12P 13/001* (2013.01); *C12P 17/182* (2013.01)

(56) References Cited

U.S. PATENT DOCUMENTS

| | | |
|---|---|---|
| 7,193,127 B1 | 3/2007 | Kutchan et al. |
| 7,390,642 B2 | 6/2008 | Kutchan et al. |
| 7,514,251 B2 | 4/2009 | Kutchan et al. |
| 7,767,428 B2 | 8/2010 | Kutchan et al. |
| 8,975,063 B2 | 3/2015 | Smolke et al. |
| 9,322,039 B2 | 4/2016 | Smolke et al. |
| 9,376,696 B1 | 6/2016 | Smolke et al. |
| 9,534,241 B2 | 1/2017 | Smolke et al. |
| 10,017,799 B2 | 7/2018 | Smolke et al. |
| 2005/0106588 A1 | 5/2005 | Kutchan et al. |
| 2005/0139490 A1 | 6/2005 | Chou et al. |
| 2005/0277179 A1 | 12/2005 | Takai et al. |
| 2006/0185032 A1 | 8/2006 | Kutchan et al. |
| 2007/0199090 A1 | 8/2007 | Apuya et al. |
| 2008/0176754 A1 | 7/2008 | Smolke et al. |
| 2008/0196123 A1 | 8/2008 | Kutchan et al. |
| 2010/0075385 A1 | 3/2010 | Kutchan et al. |
| 2014/0273109 A1 | 9/2014 | Smolke et al. |
| 2015/0267233 A1 | 9/2015 | Smolke et al. |
| 2016/0319314 A1 | 11/2016 | Smolke et al. |
| 2018/0163212 A1 | 6/2018 | Smolke et al. |

FOREIGN PATENT DOCUMENTS

| | | |
|---|---|---|
| JP | H05504252 A | 7/1993 |
| WO | WO-0058333 A1 | 10/2000 |
| WO | WO-02101052 A2 | 12/2002 |
| WO | WO-2005021763 A2 | 3/2005 |
| WO | WO-2006015887 A2 | 2/2006 |
| WO | WO-2008067070 A2 | 6/2008 |
| WO | WO-2008153094 A1 | 12/2008 |
| WO | WO-2011058446 A2 | 5/2011 |
| WO | WO-2012039438 A1 | 3/2012 |
| WO | WO-2014143744 A2 | 9/2014 |
| WO | WO-2015066642 A1 | 5/2015 |

OTHER PUBLICATIONS

Kanokarn Kocharin. PhD Thesis, Metabolic Engineering of *Saccharomyces cerevisiae* for Polyhydroxybutyrate Production. Chalmers University of Technology. Goteborg, Sweden. Apr. 2013.

Notice of allowance dated Oct. 14, 2016 for U.S. Appl. No. 14/211,611.
Notice of allowance dated Nov. 18, 2016 for U.S. Appl. No. 14/211,611.
Office action dated Jul. 25, 2016 for U.S. Appl. No. 14/211,611.
Allen et al., "RNAi-Mediated Replacement of Morphine with the Nonnarcotic Alkaloid Reticuline in Opium Poppy", Nat. Biotechnol. (2004), 22:1559-1566.
Backes et al., "Organization of Multiple Cytochrome P450s with NADPH-Cytochrome P450 Reductase in Membranes", Pharmacol. Ther. (2003), 98:221-233.
Bayer et al., "Synthesis of Methyl Halides from Biomass Using Engineered Microbes", J. Am. Chem. Soc. (2009), 131:6508-6515.
Branden et al. Introduction to Protein Structure, Garland Publishing Inc., New York, p. 247, 1991.
Bruce et al., "Microbial Degradation of the Morphine Alkaloids. Purification and Characterization of Morphine Dehydrogenase from Pseudomonas putida M10", Biochem. J. (1991), 274(3):875-880.
Choi et al., "Molecular Cloning and Characterization of Coclaurine N-Methyltransferase from Cultured Cells of Coptis japonica", J. Biol. Chem. (2002), 277:830-835.
Cooper et al., "On the amine oxidases of Klebsiella aerogenes strain W70," FEMS Microbiol. Lett.,146(1):85-89 (1997).
Co-pending U.S. Appl. No. 15/139,263, filed Apr. 26, 2016.
Dumas et al., "11 Beta-Hydroxylase Activity in Recombinant Yeast Mitochondria. In vivo Conversion of 11-Deoxycortisol to Hydrocortisone", Eur. J. Biochem. (1996), 238:495-504.
Facchini et al., "Differential and Tissue-Specific Expression of a Gene Family for Tyrosine/Dopa Decarboxylase in Opium Poppy," J. Biol. Chem., 269(43):26684-26690 (1994).
Fisinger et al., "Thebaine Synthase: a New Enzyme in the Morphine Pathway in Papaver somniferum", Natural Product Communications (2007), 2(3):249-253.
French et al., "Biological Production of Semisynthetic Opiates Using Genetically Engineered Bacteria", Biotechnology (N Y) (1995), 13:674-676.
Geissler et al., "Molecular Modeling and Site-Directed Mutagenesis Reveal the Benzylisoquinoline Binding Site of the Short-Chain Dehydrogenase/Reductase Salutaridine Reductase", Plant Physiol. (2007), 143(4):1493-503.
Grothe et al., "Molecular Characterization of the Salutaridinol 7-0-Acetyltransferase Involved in Morphine Biosynthesis in Opium Poppy *Papaver somniferum*", J. Biol. Chem. (2001), 276:30717-30723.
Hagel et al., "Benzylisoquinoline Alkaloid Metabolism: a Century of Discovery and a Brave New World", Plant Cell Physiol. (2013), 54:647-672.
Hawkins et al., "Production of Benzylisoquinoline Alkaloids in *Saccharomyces cerevisiae*", Nature Chemical Biology (2008), 4:564-573.
Hiroi et al., "Dopamine Formation from Tyramine by CYP2D6," Biochemical & Biophysical Research Communications, 249:838-843 (1998).
Ikezawa et al., "Molecular Cloning and Characterization of CYP719, a Methylenedioxy Bridge-Forming Enzyme that Belongs to a Novel P450 Family, from Cultured Coptis japonica Cells", J. Biol. Chem. (2003), 278:38557-38565.
Ikezawa et al., "Molecular Cloning and Characterization of Methylenedioxy Bridge-Forming Enzymes Involved in Stylopine Biosynthesis in Eschscholzia californica", FEBS J. (2007), 274:1019-1035.
International search report and written opinion dated Sep. 15, 2015 for PCT Application No. PCT/US2014/027833 (with publication).
International Search Report for PCT/US07/81974, dated Jul. 8, 2008.
Jensen et al., "Plant NADPH-Cytochrome P450 Oxidoreductases", Phytochemistry (2010). 71:132-141.
Kushnirov, "Rapid and Reliable Protein Extraction from Yeast", Yeast (2000), 16:857-860.
Kutchan et al., "Molecular Genetics of Plant Alkaloid Biosynthesis," Alkaloids, 50:257-316 (1998).
Kutchan, Tony M. "Heterologous expression of alkaloid biosynthetic genes—a review", Gene, vol. 179, No. 1, Nov. 7, 1996, pp. 73-81.

(56) References Cited

OTHER PUBLICATIONS

Larkin et al., "Increasing Morphinan Alkaloid Production by Over-Expressing Codeinone Reductase in Transgenic Papaver somniferum", Plant Biotechnol. J. (2007), 5:26-37.
Lenz et al., "Acetyl Coenzyme A:Salutaridinol-7-O Acetyltransferase from Papaver somniferum Plant Cell Cultures", J. Biol. Chem. (1995), 270:31091-31096.
Lenz et al., "Purification and Properties of Codeinone Reductase (NADPH) from Papaver somniferum Cell Cultures and Differentiated Plants", Eur. J. Biochem. (1995), 233:132-139.
Iragui et al., "Characterisation of *Saccharomyces cerevisiae* AR08 and AR09 genes encoding aromatic aminotransferases I and II reveals a new aminotransferase subfamily," MoL Gen. Genet., 257(2):238-248 (1998).
Moerner et al., "Illuminating single molecules in condensed matter," Science, 283(5408):1670-1676 (1999).
Morishige et al., "Molecular Characterization of the Sadenosyl-L-Methionine:3'-Hydroxy-N-Methylcoclaurine 4'O-Methyltransferase Involved in Isoquinoline Alkaloid Biosynthesis in Coptis japonica", J. Biol. Chem. (2000), 275:23398-23405.
Notice of allowance dated Mar. 8, 2016 for U.S. Appl. No. 14/614,484.
Notice of allowance dated Apr. 25, 2016 for U.S. Appl. No. 14/961,662.
Notice of allowance dated Nov. 7, 2014 for U.S. Appl. No. 11/875,814.
Office action dated Nov. 6, 2015 for U.S. Appl. No. 14/614,484.
Office action dated Dec. 10, 2015 for U.S. Appl. No. 14/211,611.
Office action dated Feb. 18, 2009 for U.S. Appl. No. 11/875,814.
Office action dated May 23, 2014 for U.S. Appl. No. 11/875,814.
Office action dated Dec. 3, 2013 for U.S. Appl. No. 11/875,814.
Office action dated Dec. 29, 2009 for U.S. Appl. No. 11/875,814.
Ounaroon et al., "(R,S)-Reticuline 7-0-Methyltransferase and (R,S)-Norcoclaurine 6-0-Methyltransferase of Papaver somniferum-cDNA Cloning and Characterization of Methyl Transfer Enzymes of Alkaloid Biosynthesis in Opium Poppy", Plant J. (2003), 36:808-819.
Samanani et al., "Molecular cloning and characterization of norcoclaurine synthase, an enzyme catalyzing the first committed step in benzylisoquinoline alkaloid biosynthesis," Plant J., 40(2):302-313 (2004).
Sandig et al., "Regulation of Endoplasm is Reticulum Biogenesis in Response to Cytochrome P450 Overproduction", Drug Metab. Rev. (1999), 31:393-410.
Sato et al., "Purification and Characterization of S-adenosyl-L-methionine: norcoclaurine 6-0-methyltransferase from Cultured Coptis japonica Cells", Eur. J. Biochem. (1994), 225:125-131.
Siddiqui et al., "Advancing Secondary Metabolite Biosynthesis in Yeast with Synthetic Biology Tools", FEMS Yeast Res. (2012), 12:144-170.
Single Molecule Detection and Manipulation Workshop. Apr. 17-18, 2000. Retrieved from http://www.nigms.nih.govinnews/reports/single_molecules.html.
Stewart et al., "A Chemist's Perspective on the Use of Genetically Engineered Microbes as Reagents for Organic Synthesis," Biotechnology and Genetic Engineering Reviews, 14:67-143 (1997).
Unterlinner et al., "Molecular Cloning and Functional Expression of Codeinone Reductase: the Penultimate Enzyme in Morphine Biosynthesis in the Opium Poppy *Papaver somniferum*", Plant J. (1999), 18:465-475.
U.S. Appl. No. 14/961,662 , filed Dec. 7, 2015.
Vuralhan et al., "Identification and characterization of phenylpyruvate decarboxylase genes in *Saccharomyces cerevisiae*," AppL Environ. Microbiol., 69(8):4534-4541 (2003).
Zenk et al., "Benzylisoquinoline Biosynthesis by Cultivated Plant Cells and Isolated Enzymes, Journal of Natural Products, 48,(5):725-738 (1985).
Zhang et al., "14-Hydroxylation of Opiates: Catalytic Direct Autoxidation of Codeinone to 14-Hydroxycodeinone", J. Am. Chem. Soc. (2005), 127:7286-7287.
Ziegler et al., "Removal of Substrate Inhibition and Increase in Maximal Velocity in the Short Chain Dehydrogenase/Reductase Salutaridine Reductase Involved in Morphine Biosynthesis", J. Biol. Chem. (2009), 284:26758-26767.
Zimmer et al., "Protein Quality—a Determinant of the Intracellular Fate of Membrane-Bound Cytochromes P450 in Yeast", DNA Cell Biol. (1997), 16:501-514.
Alcantara et al. "Sanguinarine Biosynthesis Is Associated with the Endoplasmic Reticulum in Cultured Opium Poppy Cells after Elicitor Treatment," Plant Physiology, 138 (Apr. 22, 2005): 173-183.
Bitter, Grant A., "Heterologous Gene Expression in Yeast," Methods in Enzymology, vol. 152, pp. 673-684 (1987).
Chavez-Bejar et al. Metabolic Engineering of *Escherichia coli* for L-Tyrosine Production by Expression of Genes Coding forthe Chorismate Mutase Domain ofthe Native Chorismate Mutase-Prephenate Dehydratase and a Cyclohexadienyl Dehydrogenase from Zymomonas mobilis, Applied and Environmental Microbiology, American Society for Microbiology, US, 74.10 (Mar. 14, 2008): 3284-3290.
Co-pending U.S. Appl. No. 15/978,005, filed May 11, 2018.
European search report and search opinion dated Apr. 10, 2017 for EP Application No. 14729501.8.
French, et al. Bacterial morphinone reductase is related to Old Yellow Enzyme. Biochem J. Dec. 15, 1995;312 ( Pt 3):671-8.
French et al., Purification and Characterization of Morphinone Reductase from Pseudomonas putida M10. Biochem. J. 301.1 (1994): 97-103.
Fukuda et al. Breeding of Brewing Yeast Producing a Large Amount of Beta-Phenylethyl Alcohol and Beta-Phenylethyl Acetate. Agricultural and Biological Chemistry, Tokyo, Japan, 54.1 (1990): 269-271.
Fukuda et al. Feedback-Insensitive Mutation of 3-Deoxy-D-Arabino-Hepturosonate-7-Phosphate Synthase Caused by a Single Nucleotide Substitution of ARO4 Structural Gene in *Saccharomyces cerevisiae*. Journal of Fermentation and Bioengineering, 74.2 (1992): 117-119.
Fukuda et al. Molecular Breeding of a Sake Yeast with a Mutated AR04 Gene Which Causes Both Resistance to o-Fluoro-DL-Phenylalanine and Increased Production of Beta-Phenethyl Alcohol. Journal of Fermentation and Bioengineering, 73.5 (1992): 366-369.
Gustafsson et al. Codon bias and heterologous protein expression. Trends in Biotechnology, 22.7 (Jul. 2004): 346-353.
Hartmann et al. Evolution of feedback-inhibited beta/alpha barrel isoenzymes by gene duplication and a single mutation. PNAS 100.3 (Feb. 4, 2003): 862-867.
Hawkins et al. "Supplementary Text and Figures. Production of benzylisoquinoline alkaloids in *Saccharomyces cerevisiae*," Nature Chemical Biology, Aug. 10, 2008, 15 pages.
Hawkins, K. Metabolic Engineering of *Saccharomyces cerevisiae* for the Production Of Benzylisoquinoline Alkaloids. Ph.D. Thesis, California Institute of Technology, Pasadena, California, 2009, pp. 1-154.
Hinnen et al, in: Yeast Genetic Engineering, Barr et al. eds, Butterworths (1989); (Hinnen et al. "Chapter 10: Heterologous Gene Expression in Yeast," Yeast Genetic Engineering, Barr et al. eds., Butterworths, pp. 193-213 (1989)).
Lee et al. Bacillus licheniformis APase I gene promoter: a strong well-regulated promoter in B. Subtilis. Journal of General Microbiology, 137 (1991): 1127-1133.
Lee et al. Metabolic engineering of microorganisms: general strategies and drug production. Drug Discovery Today, Jan. 2009; 14, 1/2,(Sep. 18, 2008): 78-88.
Lister, et al. Transformations of codeine to important semisynthetic opiate derivatives by Pseudomonas putida m10. FEMS Microbiol Lett. Dec. 1, 1999;181(1):137-44.
Lutke-Eversloh et al. "L-Tyrosine production by deregulated strains of *Escherichia coli*," Applied Microbiology and Biotechnology, Springer, Berlin, DE, 75.1 (Jan. 13, 2007): 103-110.
Lutke-Eversloh et al. "Perspectives of biotechnological production of L-tyrosine and its applications," Applied Microbiology and Biotechnology, Springer, Berlin, DE, 77.4 (Oct. 30, 2007): 751-762.
Luttik et al. Alleviation of feedback inhibition in *Saccharomyces cerevisiae* aromatic amino acid biosynthesis: Quantification of metabolic impact. Metabolic Engineering, 10 (2008): 141-153.

(56) References Cited

OTHER PUBLICATIONS

Minami et al., Microbial Production of Plant Benzylisoquinoline Alkaloids. Proc. Natl. Acad. Sci. U S A 105 (2008): 7393-7398.
Olson et al. Production of tyrosine from sucrose or glucose achieved by rapid genetic changes to phenylalanine-producing *Escherichia coli* strains. Applied Microbiology and Biotechnology, 74.5 (Jan. 11, 2007): 1031-1040.
Rueffer et al. (S)-Norlaudanosoline Synthase—The 1 st Enzyme in the Benzylisoquinoline Biosynthetic-Pathway. FEBS Letters, 129.1 (Jun. 1981): 5-9.
Ruohonen et al. Modifications to the ADH1 promoter of *Saccharomyces cerevisiae* for efficient production of heterologous proteins. Journal of Biotechnology, 39 (1995): 193- 203.
Schmidheini, et al., A Single Point Mutation Results in a Constitutively Activated and Feedback-Resistant Chorismate Mutase of *Saccharornyces-cerevisiae*. J Bacteriol., 171(3):1245-1253, 1989.
Schmidt et al. Poppy alkaloid profiling by electrospray tandem mass spectrometry and electrospray FT-ICR mass spectrometry after [ring-1 3C6]-tyramine feeding. Phytochemistry, 68.2 (2007): 189-202.
U.S. Appl. No. 15/139,263 Office Action dated Feb. 16, 2018.
U.S. Appl. No. 15/360,763 Notice of Allowance dated May 11, 2018.
U.S. Appl. No. 15/360,763 Office Action dated Apr. 10, 2018.
U.S. Appl. No. 15/360,763 Office Action dated Dec. 20, 2017.
U.S. Appl. No. 15/567,354 Office Action dated Jul. 19, 2018.
Vuralhan, Z. "Engineering of aromatic amino acid metabolism in *Saccharomyces cerevisiae*," Ph. D. Thesis. (Apr. 11, 2006): 1-110.
Walker, et al. Mechanistic studies of morphine dehydrogenase and stabilization against covalent inactivation. Biochem J. Feb. 1, 2000;345 Pt 3:687-92.
Willey, et al. Nucleotide sequence and over-expression of morphine dehydrogenase, a plasmid-encoded gene from Pseudomonas putida M10. Biochem J. Mar. 1, 1993;290 ( Pt 2):539-44.
U.S. Appl. No. 15/567,358 Office Action dated Sep. 17, 2018.
U.S. Appl. No. 15/139,263 Notice of Allowance dated Oct. 15, 2018.
Co-pending U.S. Appl. No. 16/191,247, filed on Nov. 11, 2018.
Co-pending U.S. Appl. No. 16/216,829, filed on Dec. 11, 2018.
U.S. Appl. No. 16/191,247 Office Action dated Jan. 15, 2019.

BIA Pathway Variations

| Sub-pathway | Substrate | Product | Example strain |
|---|---|---|---|
| A | tyrosine | dopamine | CSY235 |
| B | tyrosine | dopamine | CSY88 |
| C | tyrosine | 4-HPA | CSY104 |
| D | tyrosine | 4-HPA | CSY73 |
| E | dopamine + 4-HPA | norcoclaurine | CSY177 |
| F | norcoclaurine | reticuline | |
| G | norlaudanosoline | reticuline | CSY288 |
| H | laudanosoline | reticuline | CSY288 |
| I | reticuline | laudanine | CSY401 |
| J | reticuline | canadine | CSY410 |
| K | reticuline | thebaine | |
| L | laudanosoline | BIA #1 | |
| M | norlaudanosoline | laudanosoline | |
| N | norcoclaurine | laudanosoline | |
| O | norlaudanosoline | BIA #2 | |
| P | reticuline | BIA #3 | |
| Q | norcoclaurine | norlaudanosoline | |

FIG. 16A

Combinations of BIA sub-pathways

| Combinatorial pathway | Substrate | Product | Example strain |
|---|---|---|---|
| A + C + E + F + I | tyrosine | laudanine | |
| A + C + E + F + J | tyrosine | canadine | |
| A + C + E + F + K | tyrosine | thebaine | |
| B + C + E + F + I | tyrosine | laudanine | |
| B + C + E + F + J | tyrosine | canadine | |
| B + C + E + F + K | tyrosine | thebaine | |
| A + D + E + F + I | tyrosine | laudanine | |
| A + D + E + F + J | tyrosine | canadine | |
| A + D + E + F + K | tyrosine | thebaine | |
| B + D + E + F + I | tyrosine | laudanine | |
| B + D + E + F + J | tyrosine | canadine | |
| B + D + E + F + K | tyrosine | thebaine | |
| G + I | norlaudanosoline | laudanine | CSY401 |
| G + J | norlaudanosoline | canadine | CSY410 |
| G + K | norlaudanosoline | thebaine | |
| H + I | laudanosoline | laudanine | |
| H + J | laudanosoline | canadine | CSY410 |
| H + K | laudanosoline | thebaine | |

FIG. 16B

Example combinations of BIA sub-pathways to produce non-natural alkaloids

| Combinatorial pathway | Substrate |
|---|---|
| M + L | norlaudanosoline |
| A + C + E + N + L | tyrosine |
| A + D + E + N + L | tyrosine |
| B + C + E + N + L | tyrosine |
| B + D + E + N + L | tyrosine |
| A + C + E + Q + O | tyrosine |
| A + D + E + Q + O | tyrosine |
| B + C + E + Q + O | tyrosine |
| B + D + E + Q + O | tyrosine |
| A + C + E + F + P | tyrosine |
| A + D + E + F + P | tyrosine |
| B + C + E + F + P | tyrosine |
| B + D + E + F + P | tyrosine |
| G + P | norlaudanosoline |
| H + P | laudanosoline |

FIG. 16C

COMPOSITIONS AND METHODS FOR PRODUCING BENZYLISOQUINOLINE ALKALOIDS

CROSS-REFERENCE TO RELATED APPLICATIONS

The application is a continuation application of U.S. patent application Ser. No. 14/614,484, filed Feb. 5, 2015, which application is a divisional application of U.S. patent application Ser. No. 11/875,814, filed Oct. 19, 2007, which application claims the benefit of U.S. Provisional Application No. 60/859,149, filed Nov. 15, 2006, and U.S. Provisional Application No. 62/852,954, filed Oct. 19, 2016, each of which are incorporated by reference in their entirety.

STATEMENT REGARDING FEDERALLY SPONSORED RESEARCH OR DEVELOPMENT

This invention was made with government support under Grant No. GM077346 awarded by the National Institutes of Health. The government has certain rights in the invention.

BACKGROUND OF THE INVENTION

Field of the Invention

The invention relates to compositions and methods for producing benzylisoquinoline alkaloids (BIAs) or molecules involved in the production of BIAs. The compositions comprise host cells comprising at least one heterologous coding sequence that encodes for an enzyme or its equivalent that is involved in the BIA synthetic pathway.

Background of the Invention

Alkaloids are a diverse group of nitrogen-containing small molecules that are produced in plants, marine organisms, and microorganisms through complex biosynthetic pathways. These complex molecules exhibit a range of interesting pharmacological activities and have been used as antimalarials, anticancer agents, analgesics, and in treatment of parkinsonism, hypertension, and central nervous system disorders.

The benzylisoquinoline alkaloids (BIAs) are a family of alkaloid molecules with over 2,500 defined structures. The most common BIAs currently utilized as medicinal compounds are synthesized in the opium poppy and include the analgesics codeine and morphine. However, many intermediates in this pathway that do not accumulate to significant levels in plants are themselves pharmacologically active as analgesics, antimalarials, anticancer agents, and antimicrobial agents. Even for molecules that accumulate to high levels in plants, it would be advantageous to eliminate the rigorous extraction and purification procedures required to isolate these compounds.

Chemical synthesis of these types of molecules is normally a costly and time-consuming process, often requiring harsh process conditions, generating toxic waste streams, and resulting in low quantities of the chemicals. In addition, many structures are simply unattainable using traditional synthesis methods due to the number of chiral centers and reactive functional groups. Alternatively, the production of BIAs can be achieved at relatively low cost and high yields in a microbial host. This will allow for cost-effective large scale production of intermediate and end-product BIAs.

The inventors have developed methods and compounds for the production of complex BIAs and their intermediates. Specifically, one can generate these molecules by expressing cloned and synthetic cDNAs in the host organism such that precursor molecules naturally produced in yeast, specifically L-tyrosine, are converted to various BIA intermediates in these engineered strains through a series of specific reactions catalyzed by recombinant enzymes. Engineered yeast strains can also be used to convert more complex substrates into value-added BIA molecules using similar strategies. The novel technology developed is the production of this family of alkaloid molecules in yeast from simple precursor molecules and/or more complex substrates using yeast or another microorganism as a host for the production of these molecules. Various BIA intermediates will be produced in yeast and can be used directly for their pharmacological activities or they can be used as starting molecules for chemical synthesis modifications to place additional functional groups on these backbone molecules to alter their pharmacological activities. For instance, one important intermediate reticuline is a molecule from which a number of pharmacologically active molecules such as sanguinarine and codeine can be synthesized. In addition, host cells can be engineered to produce non-natural alkaloid derivatives by adding novel enzymatic conversion steps to the heterologous pathway or eliminating steps from the native or heterologous pathway.

Microbial biosynthesis enables green synthesis and the production of these molecules without extreme reaction conditions and toxic waste streams. Furthermore, many intermediates of interest do not accumulate in the native plant hosts, and studies have demonstrated that modifying expression of specific genes in this pathway in the native plant hosts in order to direct accumulation of specific intermediates often inactivates multiple enzymes in the pathway, prohibiting the rational engineering of plant strains to accumulate specific intermediates. Microbial biosynthesis also eliminates the need for rigorous extraction and purification procedures required to isolate target molecules from the native host.

SUMMARY OF THE INVENTION

The present invention relates to host cells that produce compounds classified as benzylisoquinoline alkaloids, as well as select precursors and intermediates thereof. The host cells comprise one, two or more heterologous coding sequences wherein each of the heterologous coding sequences encodes an enzyme involved in the metabolic pathway of a benzylisoquinoline, or its precursors or intermediates from a starting compound. The invention also relates to methods of producing the benzylisoquinoline, as well as select precursors and intermediates thereof by culturing the host cells under conditions that promote expression and activity of the necessary enzymes that produce the benzylisoquinoline or precursors or intermediates thereof, as well as optimize the growth rate of the host.

BRIEF DESCRIPTION OF THE DRAWINGS

FIG. 4A shows the pathway of norcoclaurine production and FIG. 4B shows the chromatogram confirming production of norcoclaurine.

FIG. 6A shows the levels of methyl norlaudanosoline produced, and FIG. 6B shows the levels of methyl laudanosoline produced.

FIG. 13A shows the level of canadine produced, FIG. 13B shows the level of tetrahydrocolumbamine produced, FIG. 13C shows the level of scoulerine produced, and FIG. 13D shows the level of reticuline produced. Characteristic MS/MS fragmentation patterns are also shown for each ion.

FIGS. 16A-16J depict exemplary combination and subcombination pathways of the present invention. FIGS. 16A-16C depict exemplary overall combination pathways and FIGS. 16D-16I depict the subcombination pathways including the chemical species and enzymes involved in the pathways. Pathway designations in FIGS. 16D-16I refer to the pathway designations in FIGS. 16A-16C. FIG. 16J is but one embodiment of the methods of the present invention that combines a few of the subcombination pathways to produce a BIA.

DETAILED DESCRIPTION OF THE INVENTION

Figure 1:
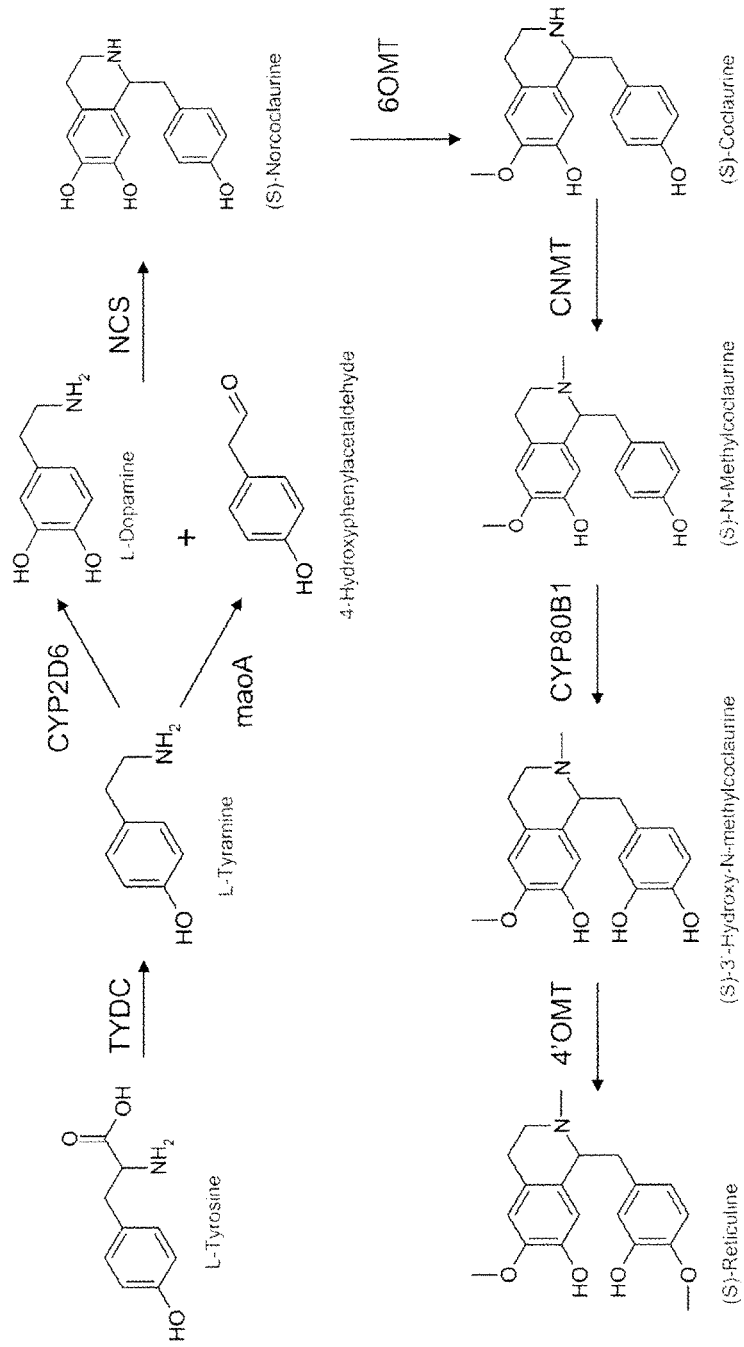
FIG. 1 depicts a synthetic pathway present in the host cells of the present invention. The pathway begins with tyrosine and ends with reticuline. The pathway can include fewer enzymes than those displayed if the desired end result is one of the intermediates in the tyrosine→reticuline pathway.
Figure 2:
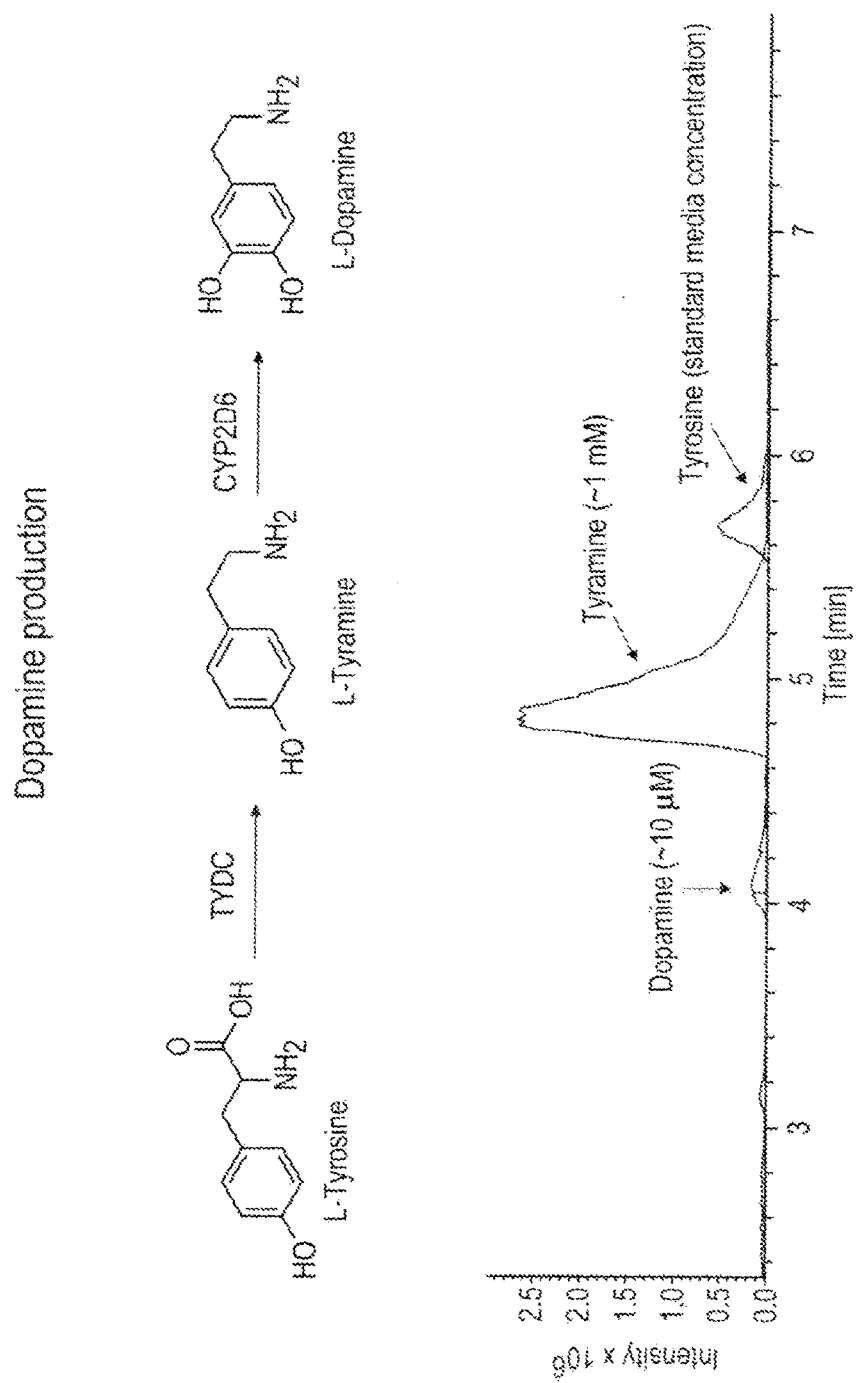
FIG. 2 depicts measurement of dopamine production from a culture of host cells of the present invention.
Figure 3:
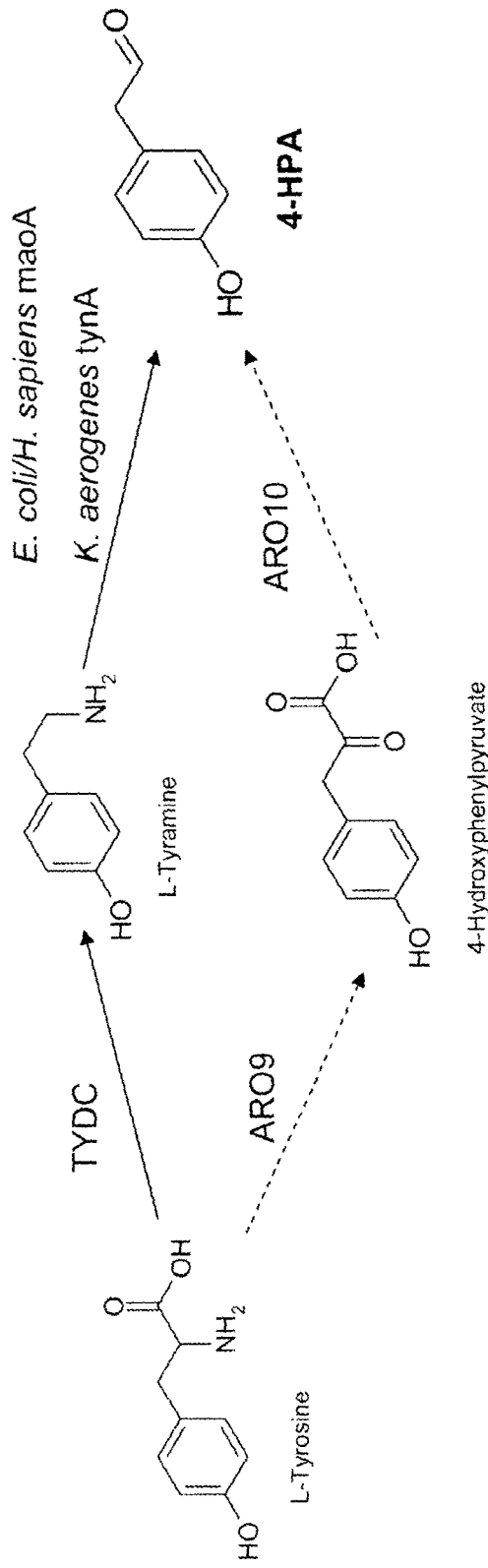
FIG. 3 depicts alternative pathways for 4-HPA production-from tyrosine through either tyramine or 4-hydroxyphenylpyruvate.
Figure 4A:
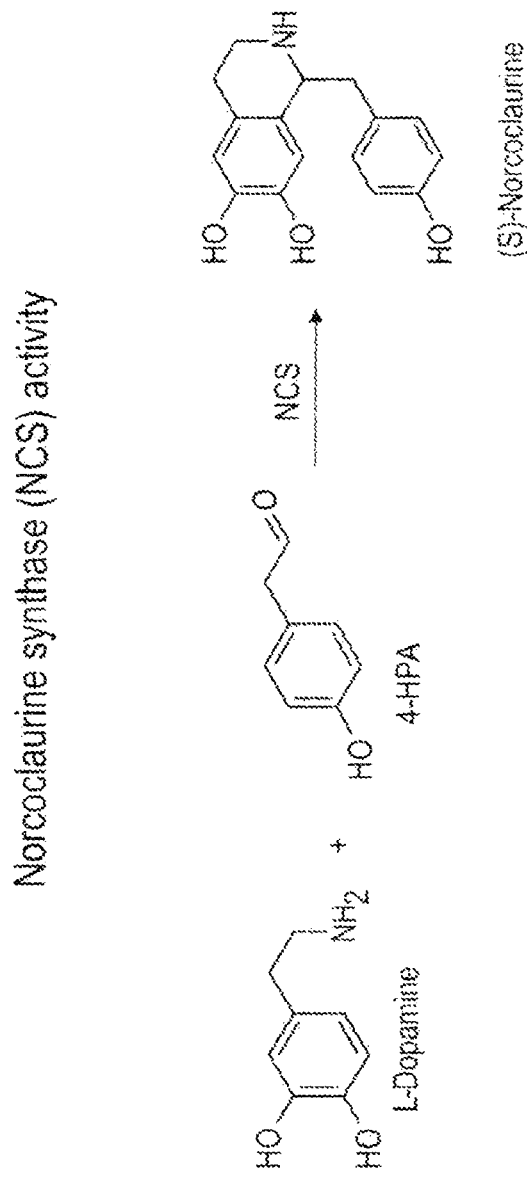
FIGS. 4A and 4B depict measurement of norcoclaurine production from a culture of host cells of the present invention. In this particular culture, the cells possessed the NCS heterologous coding sequence and the growth media was supplemented with dopamine and 4-HPA.
Figure 4B:
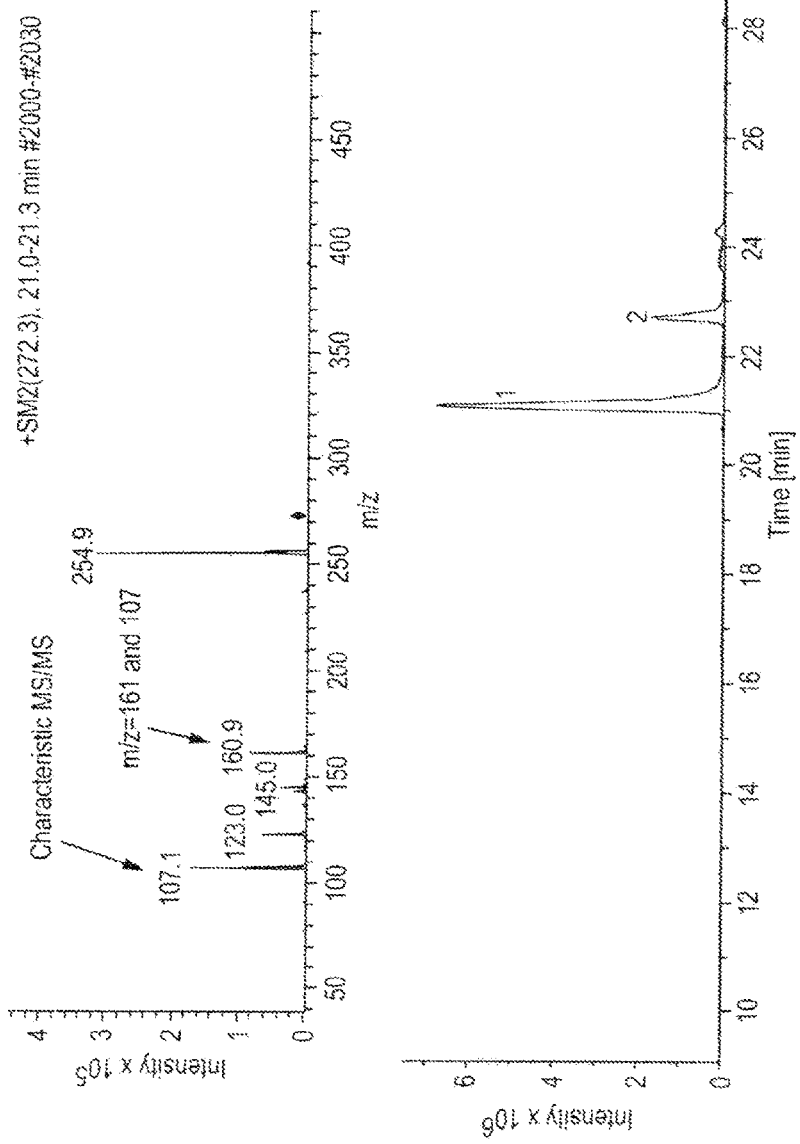
Figure 5:
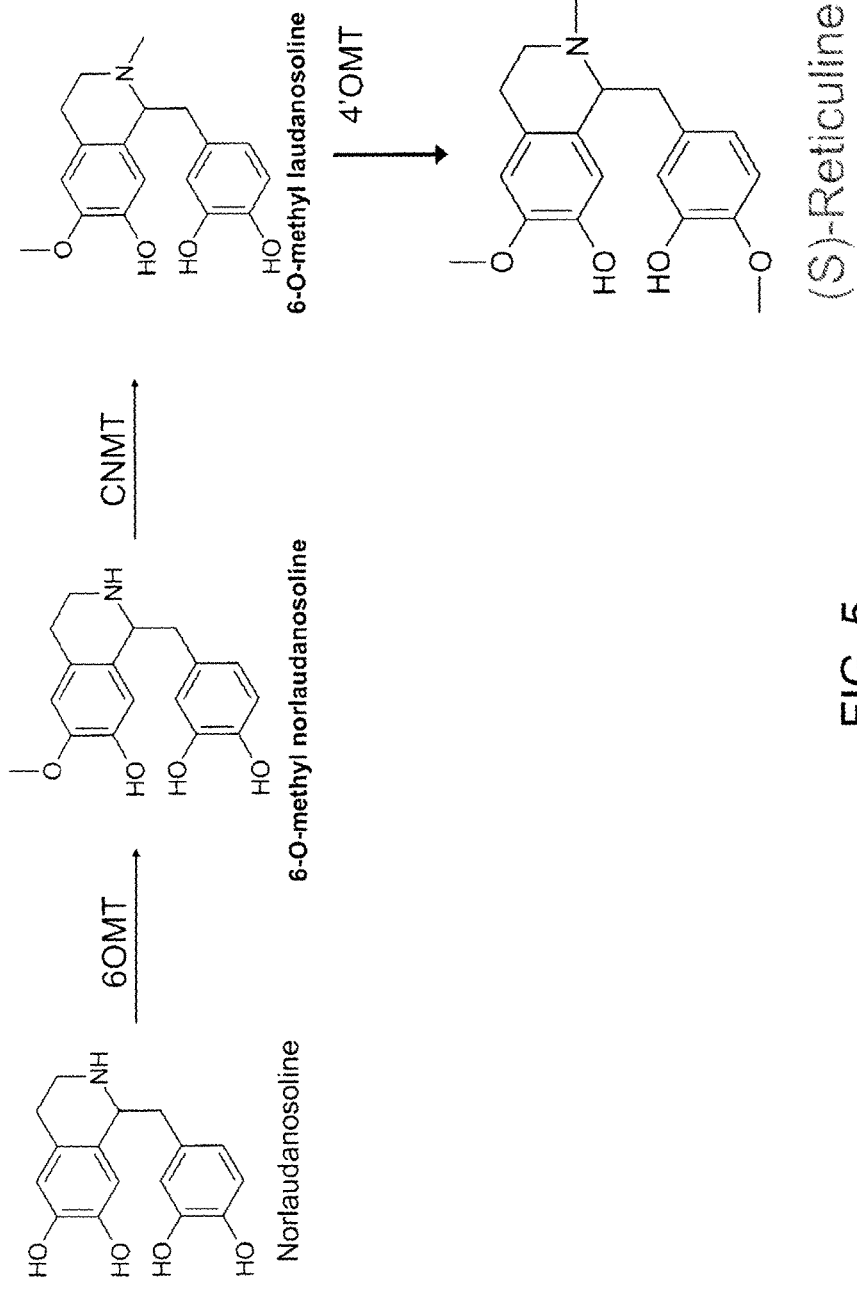
FIG. 5 depicts the synthetic pathway present in embodiments of host cells in the present invention. The pathway begins with norlaudanosoline and ends with reticuline. The pathway can include fewer enzymes than those displayed if the desired end result is one of the intermediates in the norlaudanosoline→reticuline pathway.
Figure 6A:
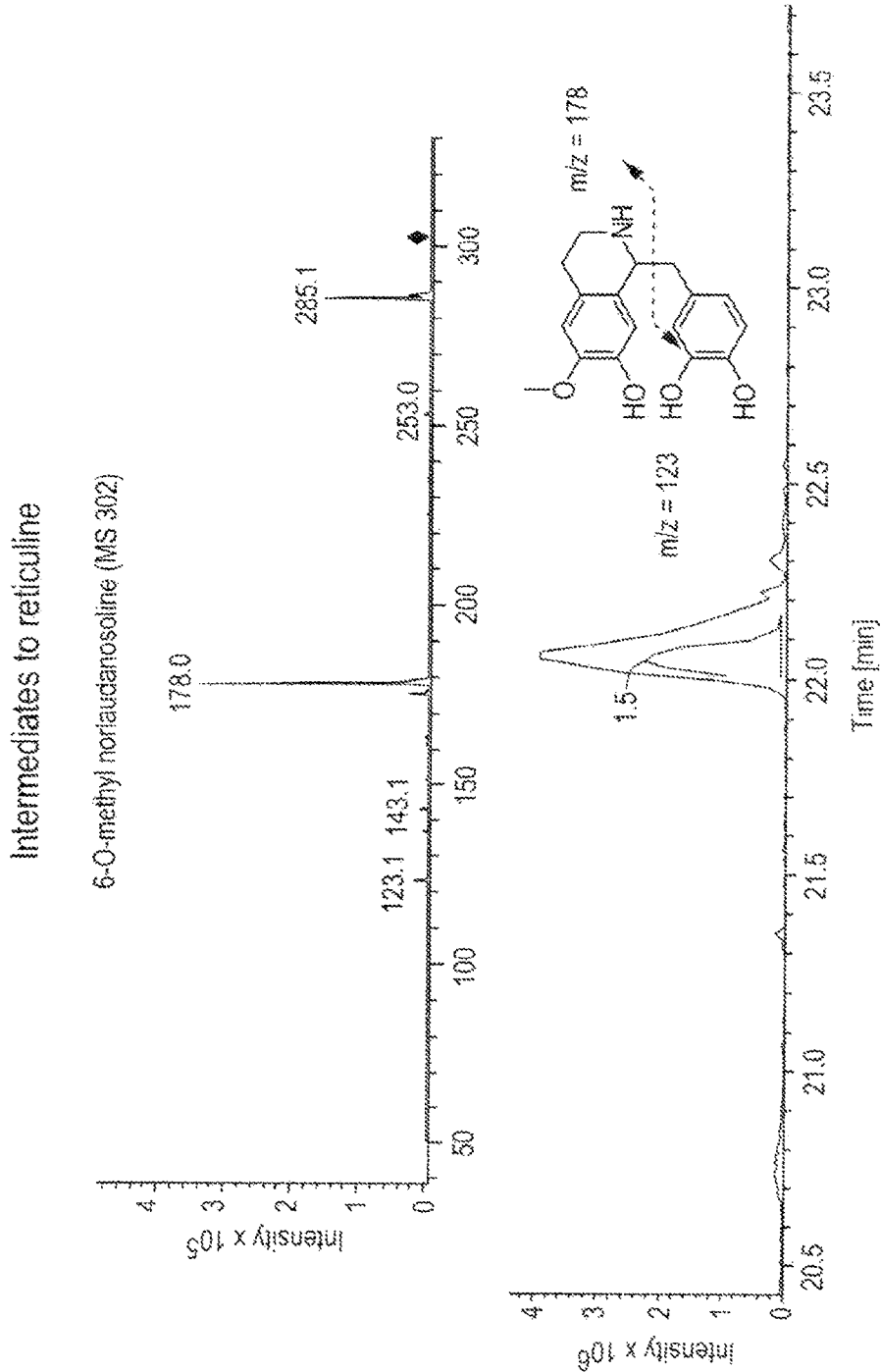
FIGS. 6A and 6B depict the measurement of intermediates in the norlaudanosoline→reticuline pathway.
Figure 6B:
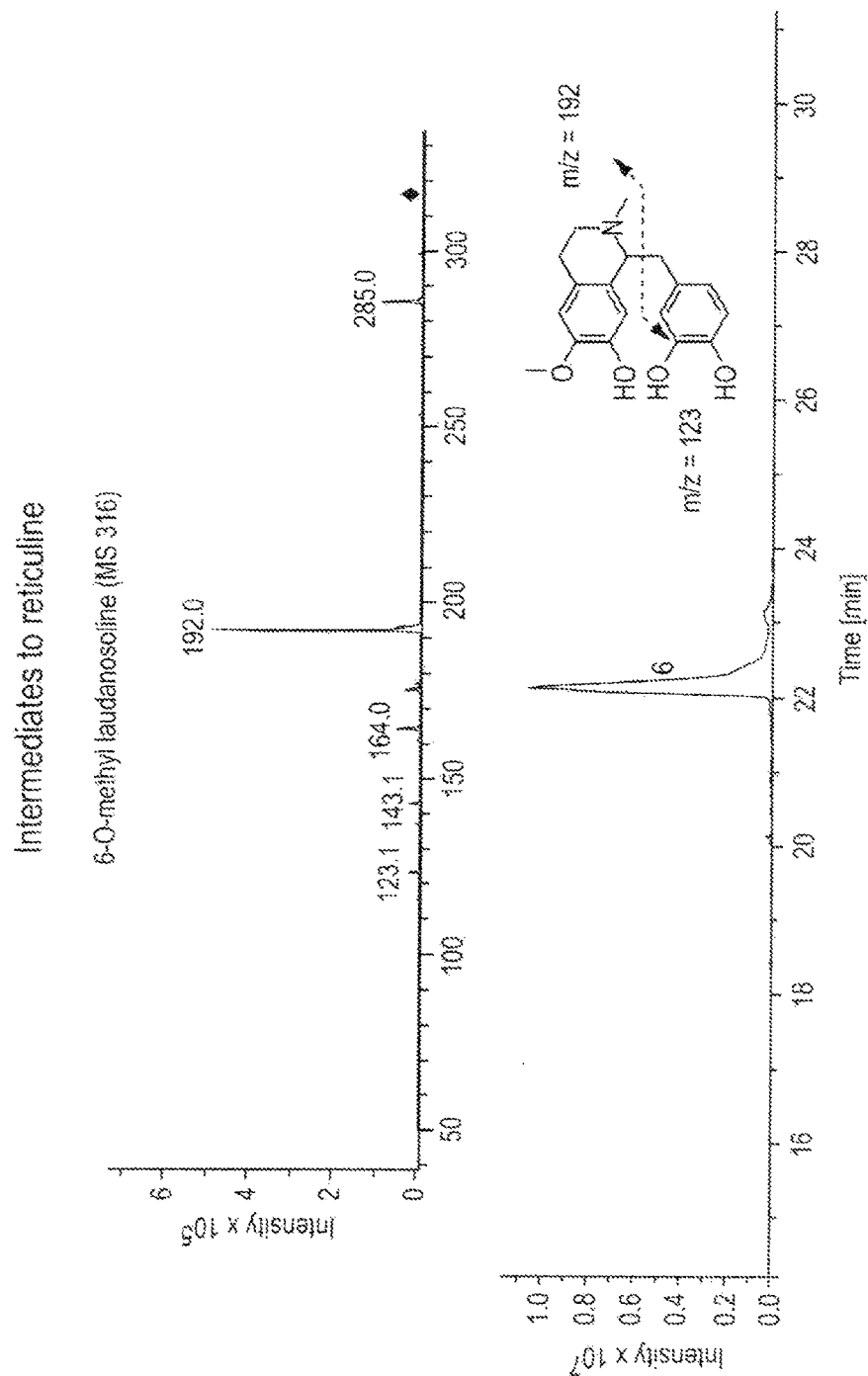
Figure 7:
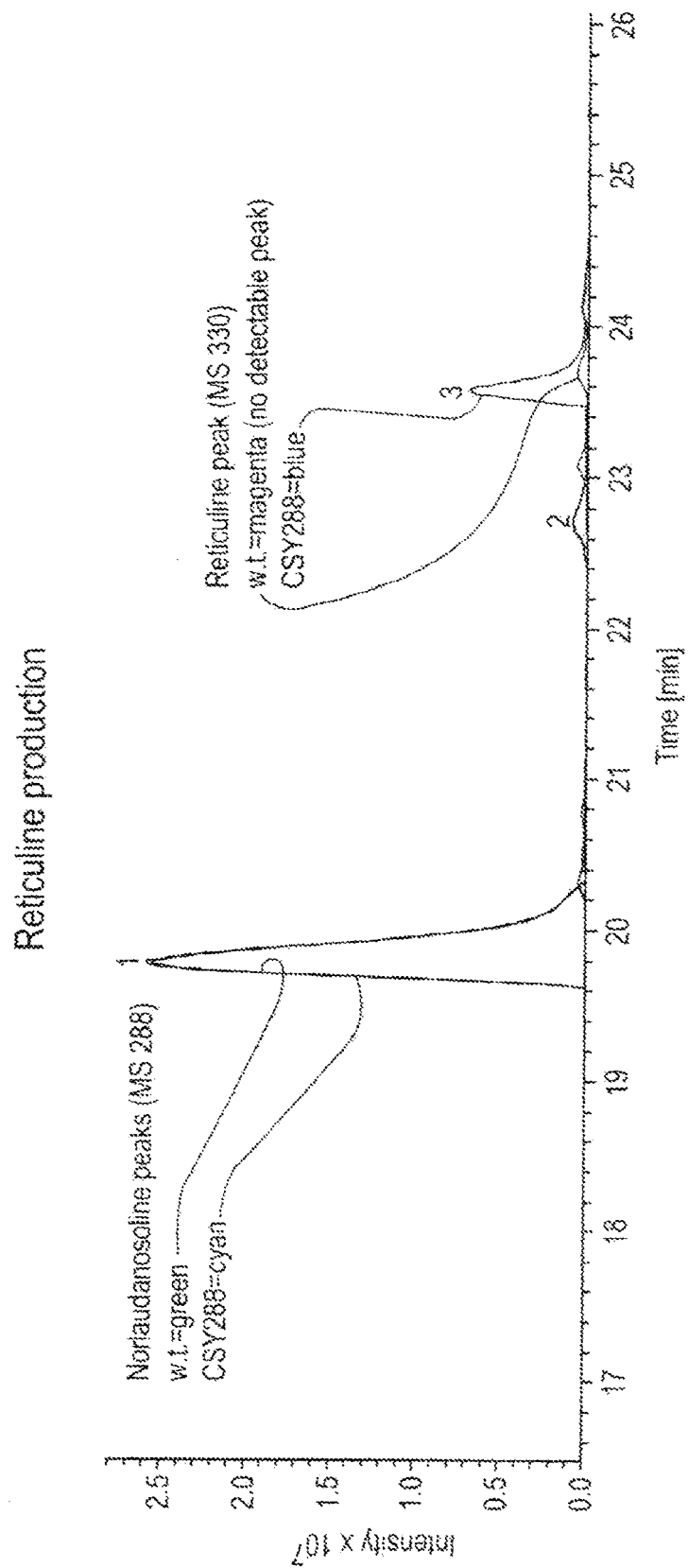
FIG. 7 depicts the measurement of reticuline from the host cells shown in FIG. 5.
Figure 8:
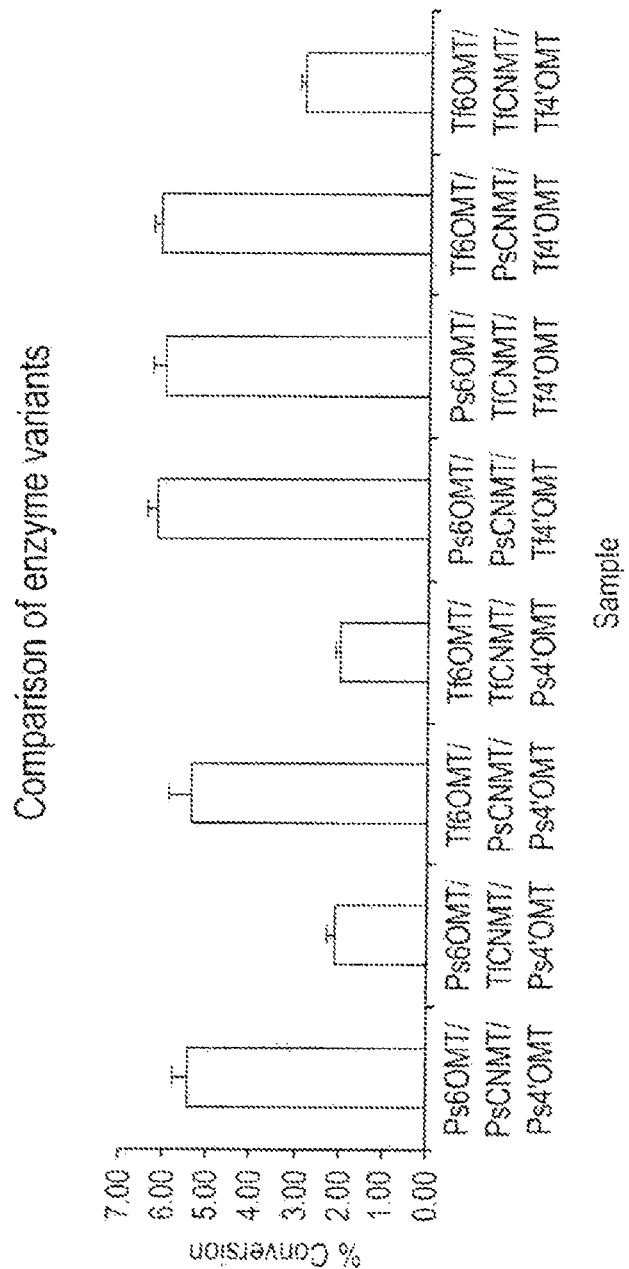
FIG. 8 depicts the levels of substrate conversion obtained from host cells expressing different coding sequences available for the enzymes of the pathway. The data demonstrate that any combination of enzyme variants (obtained from different native host sources) will produce reticuline from the substrate. However, it is observed that certain combinations produce higher levels of reticuline than others.
Figure 9:
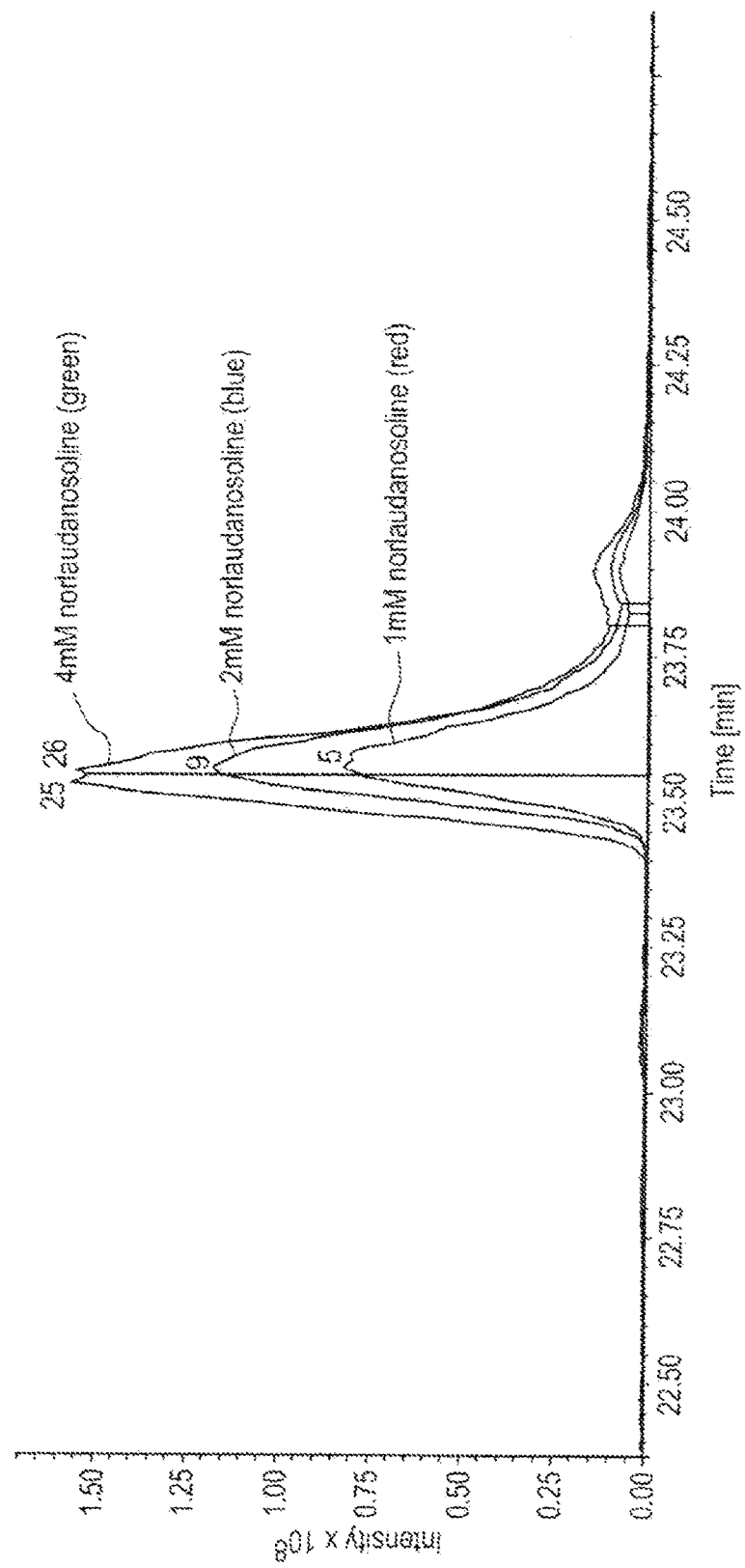
FIG. 9 depicts measurement of levels of reticuline production when fed various amounts of the starting substrate.
Figure 10:
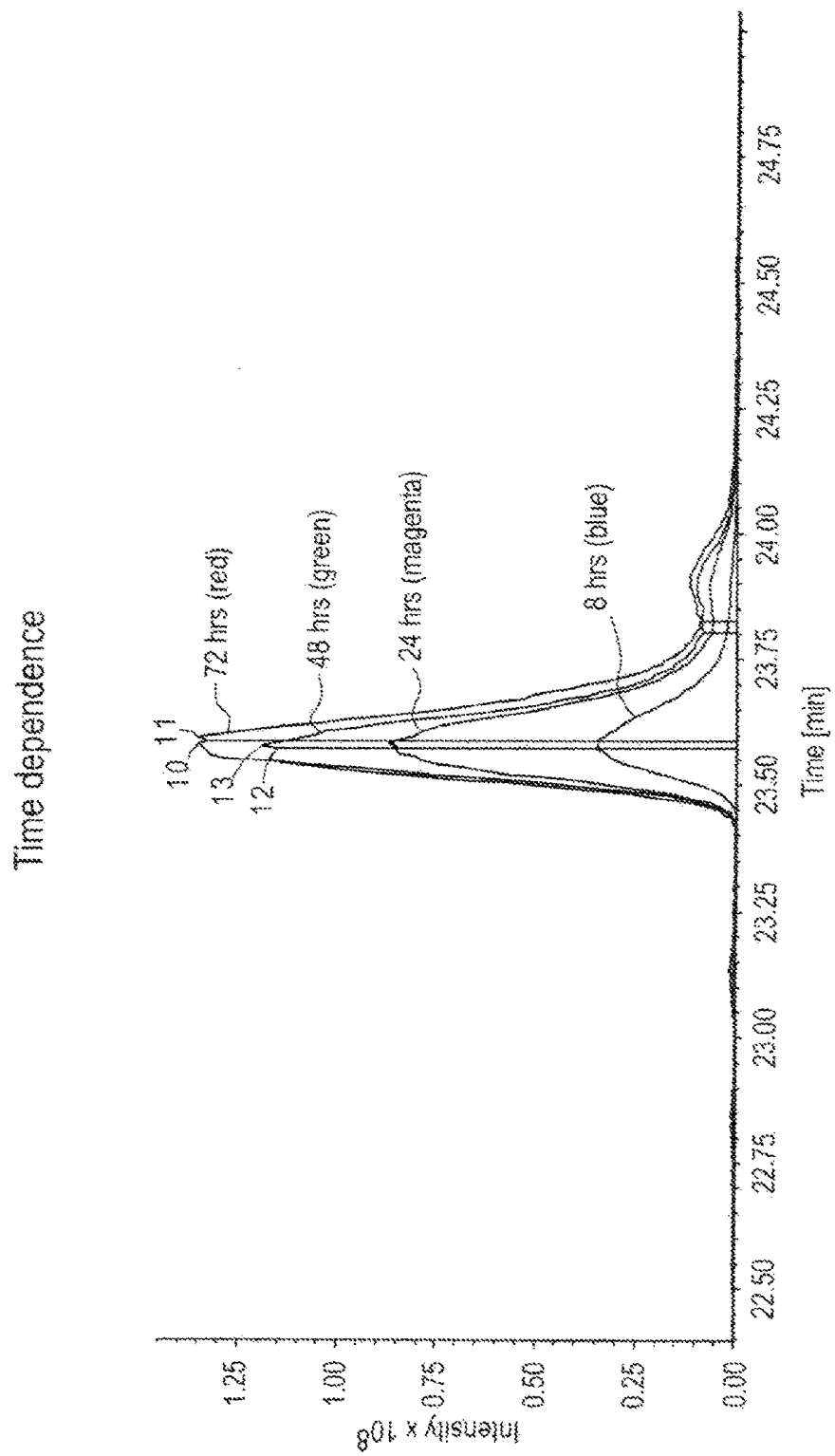
FIG. 10 depicts measurement of levels of reticuline production from the supplied substrate at various points in the growth cycle of the host cells. The data demonstrate that the cells continue to produce and accumulate reticuline well into stationary phase, suggesting different fermentation strategies for maximizing reticuline production.
Figure 11:
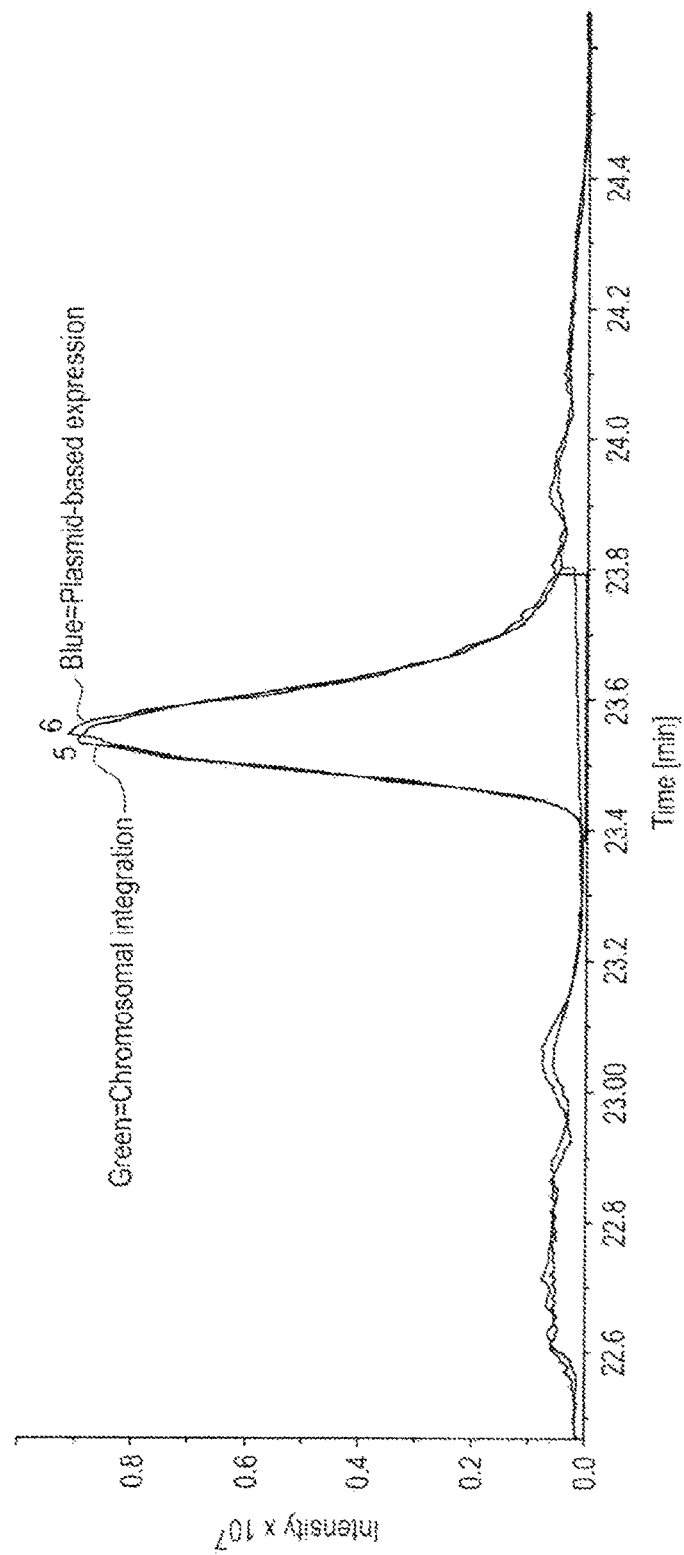
FIG. 11 depicts measurement of levels of reticuline production when the coding sequences for the heterologous enzymes are either integrated into the genome or expressed from plasmids. The data demonstrate that integration does not affect the level of accumulation of the desired BIA, confirming that the enzymes remain functional and expression is sufficient when integrated into the host genome.
Figure 12:
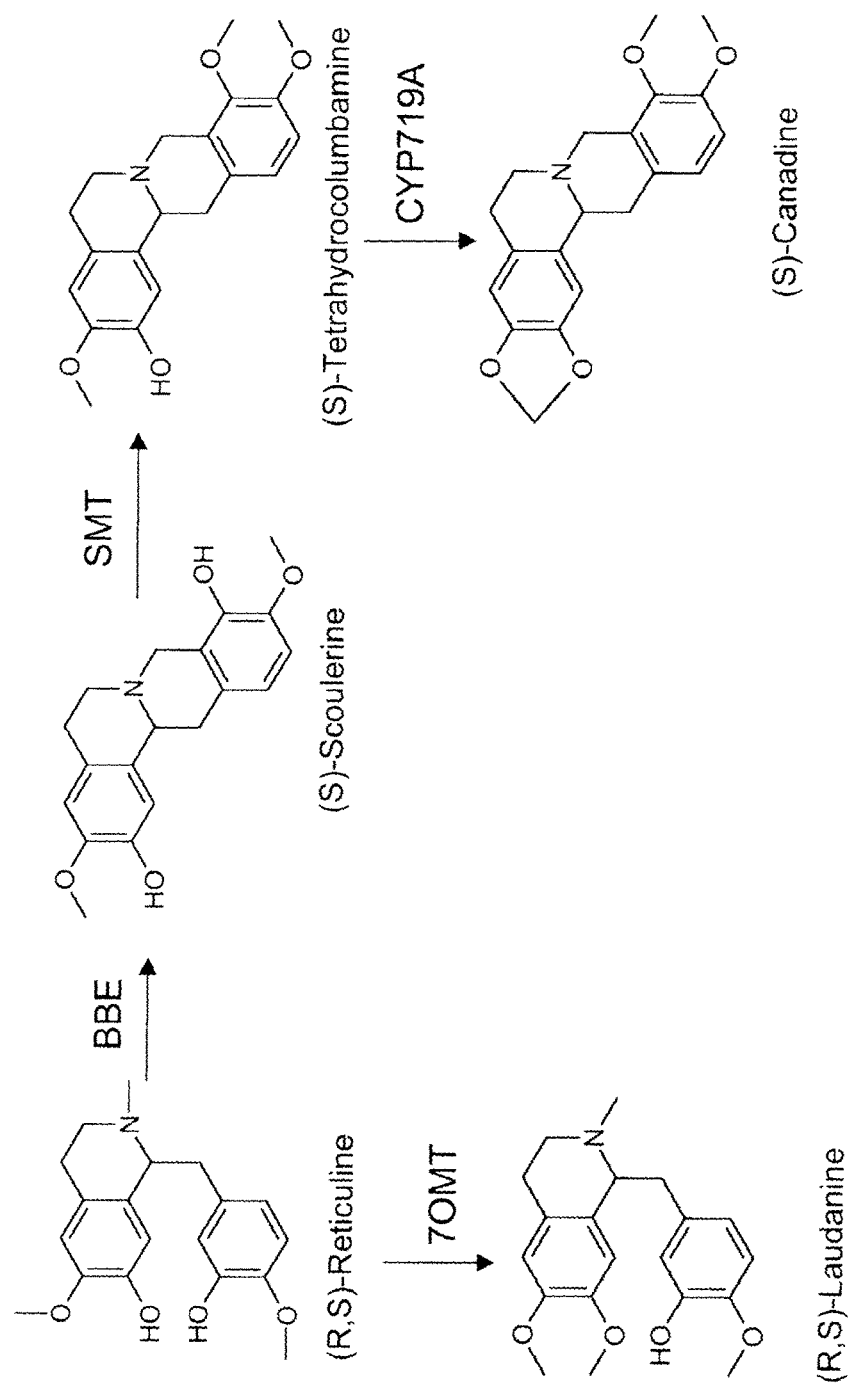
FIG. 12 depicts the synthetic pathway present in embodiments of host cells of the present invention. Although the pathway may be longer, starting from tyrosine or norlaudanosoline as shown in other figures, this particular pathway begins with reticuline and ends with either laudanine or canadine. The pathway can include fewer enzymes than those displayed if the desired end result is one of the intermediates in the norlaudanosoline→canadine pathway.
Figure 13A:
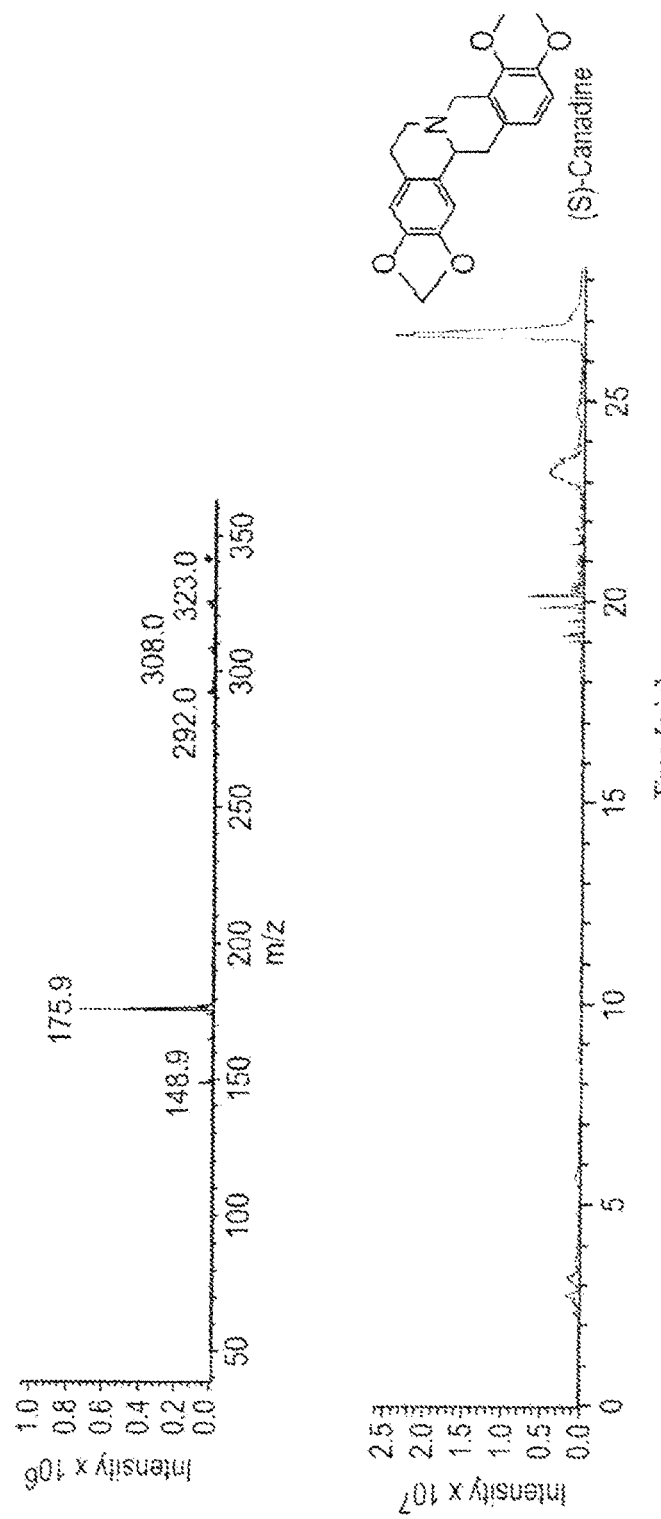
FIGS. 13A-13D depict the measurement of intermediates in the reticuline→canadine pathway.
Figure 13B:
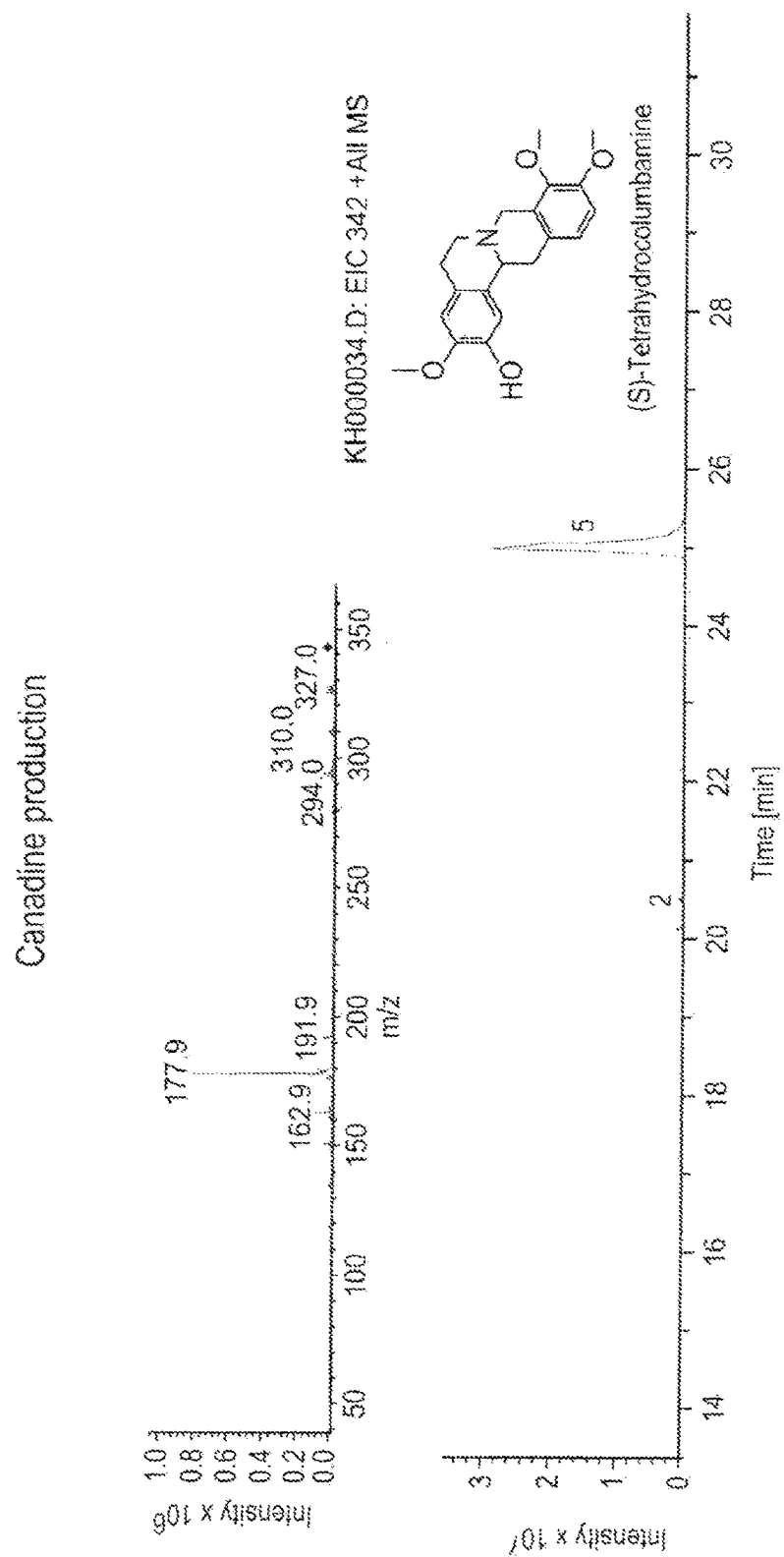
Figure 13C:
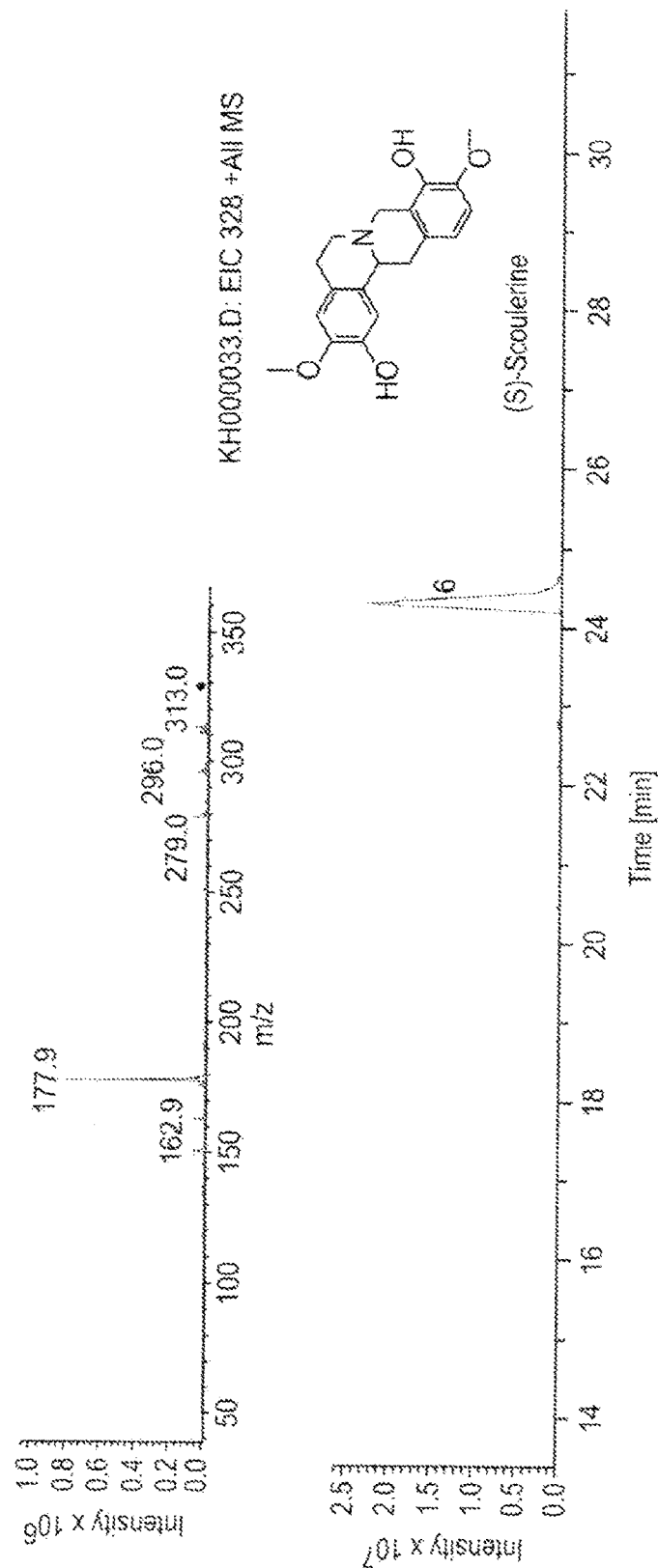
Figure 13D:
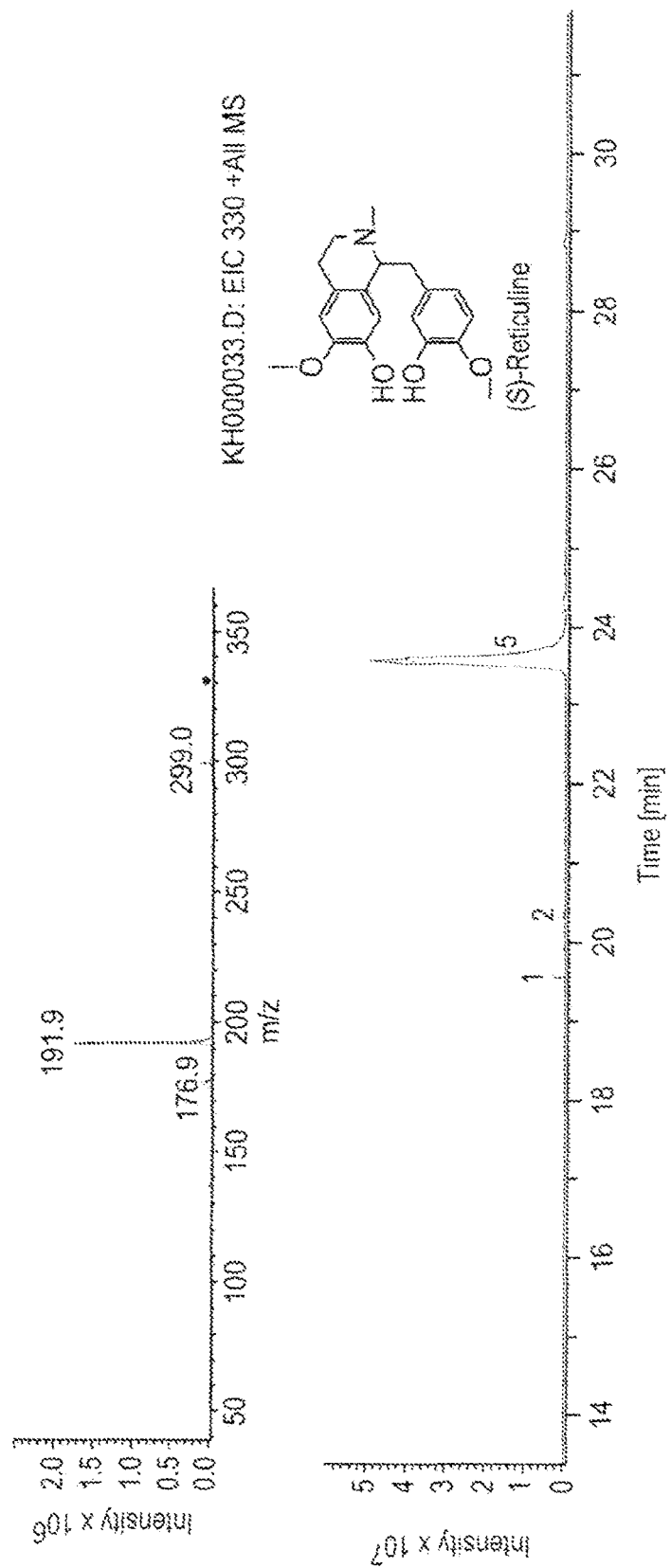
Figure 14:
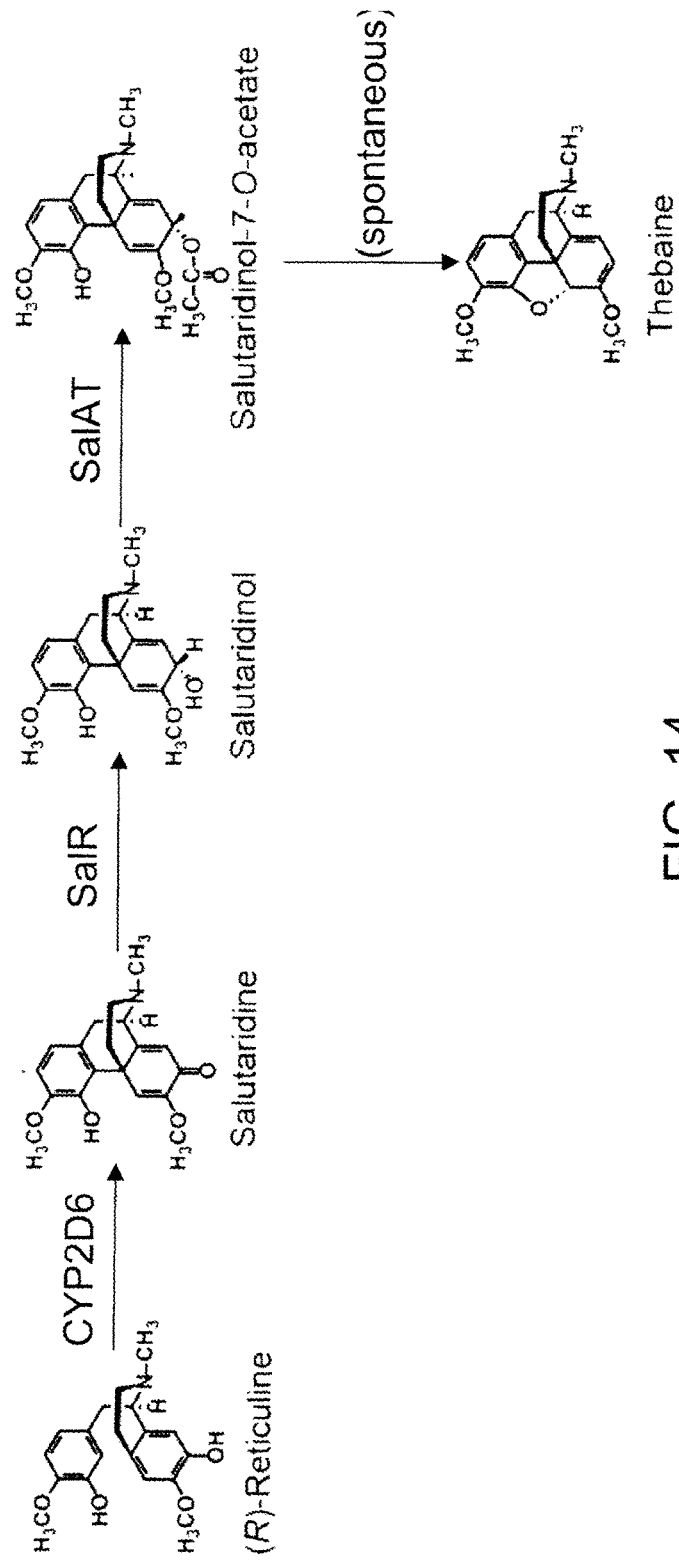
FIG. 14 depicts a synthetic pathway from reticuline to thebaine. Note that the conversion of salutaridinol-7-O-acetate to thebaine is spontaneous, thus not requiring additional enzymatic steps.
Figure 15:
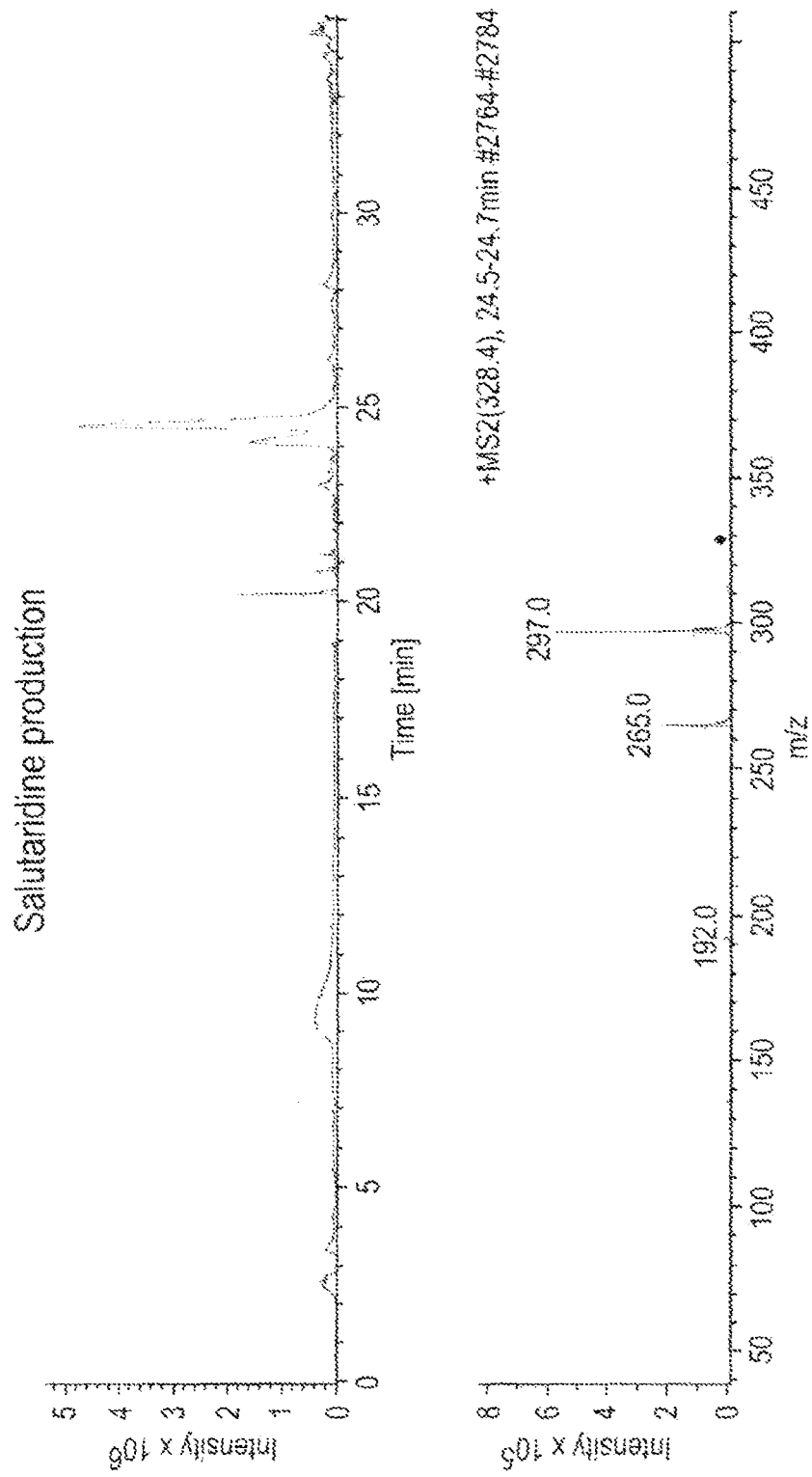
FIG. 15 depicts salutaridine production in host cells comprising heterologous sequences coding for 6OMT, CNMT, 4'OMT, yCPR1 and yCYP2D6. The pathway synthesizes salutaridine when the cells are fed laudanosoline. The characteristic MS/MS fragmentation pattern is also shown for this ion.
Figure 16D:
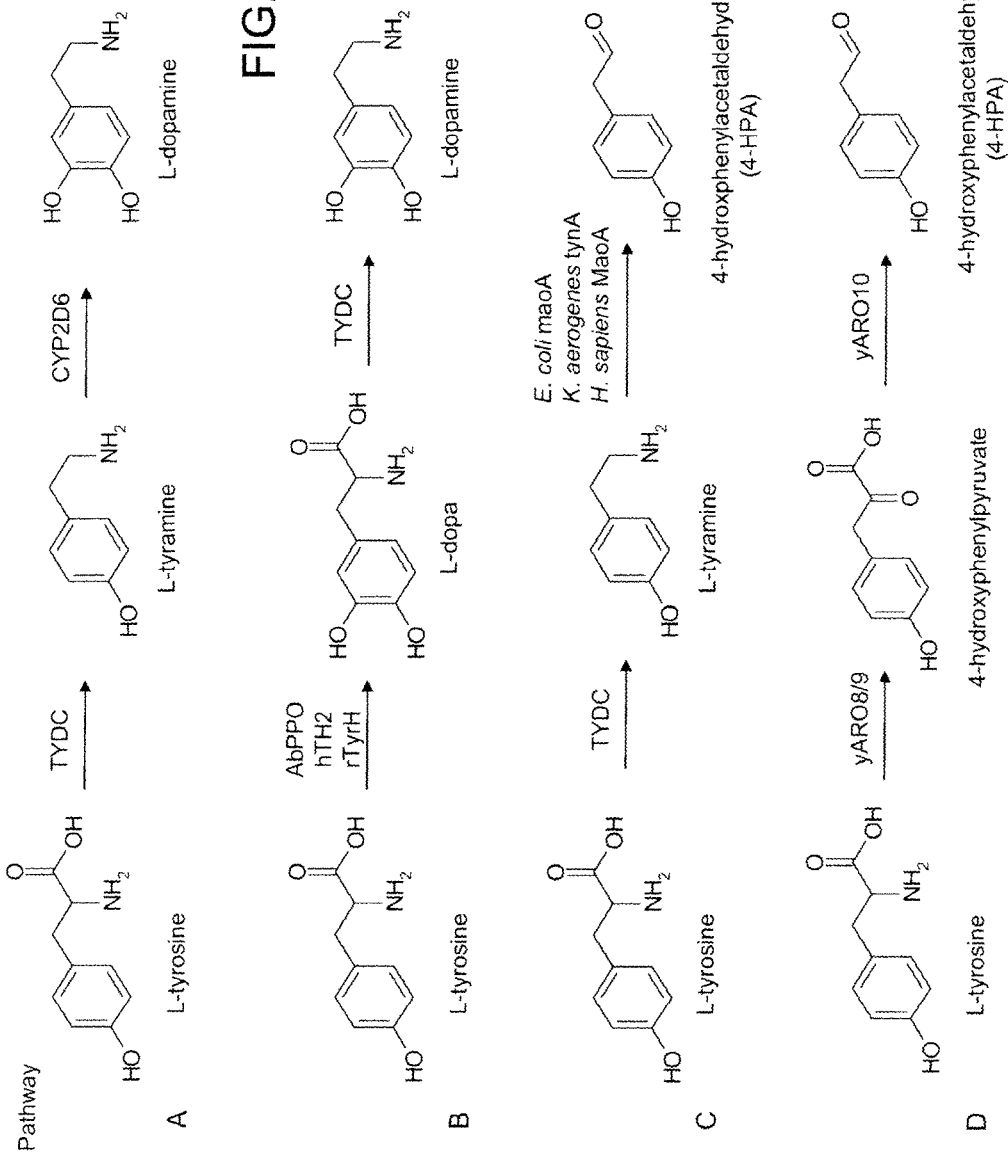
Figure 16E:
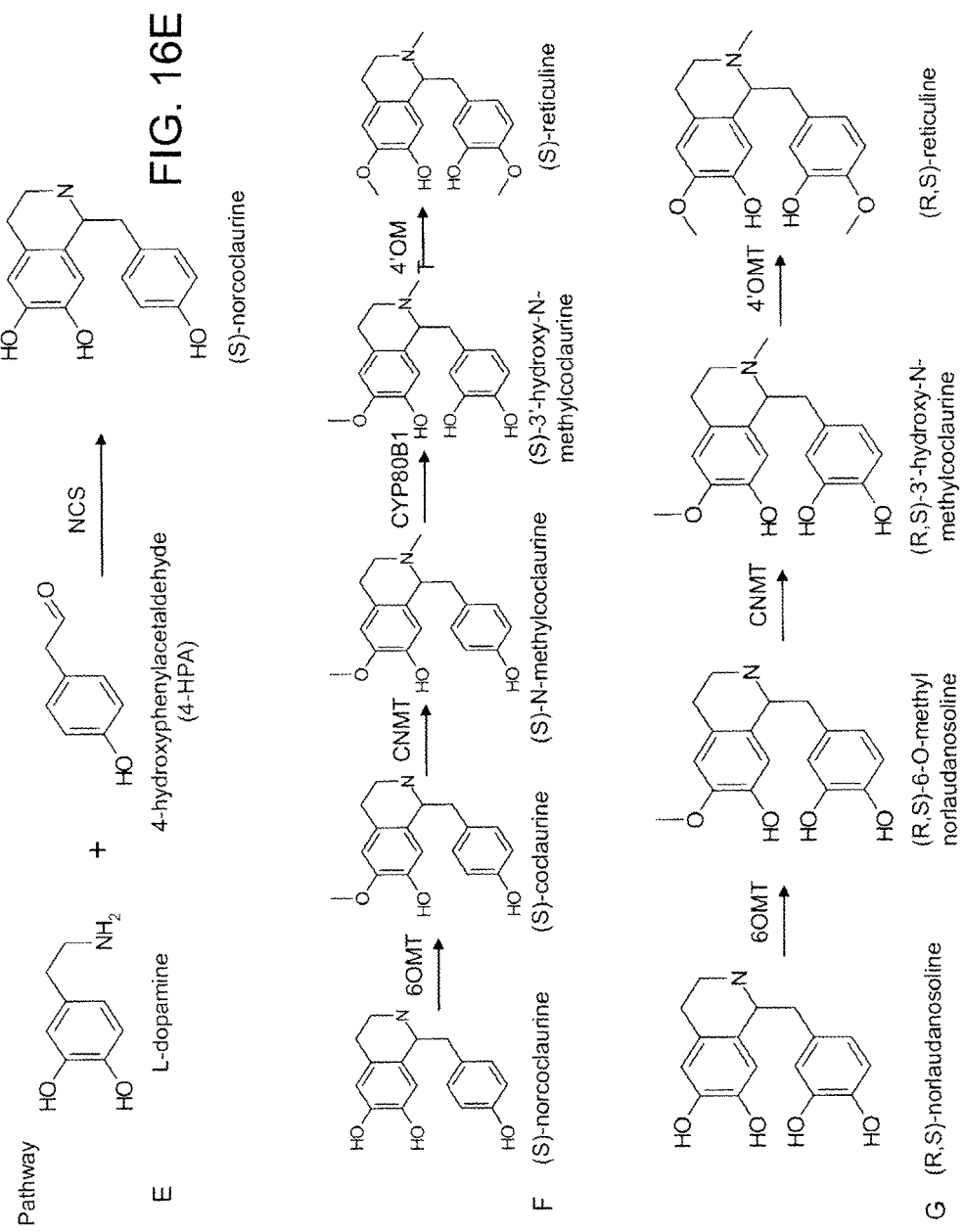
Figure 16F:
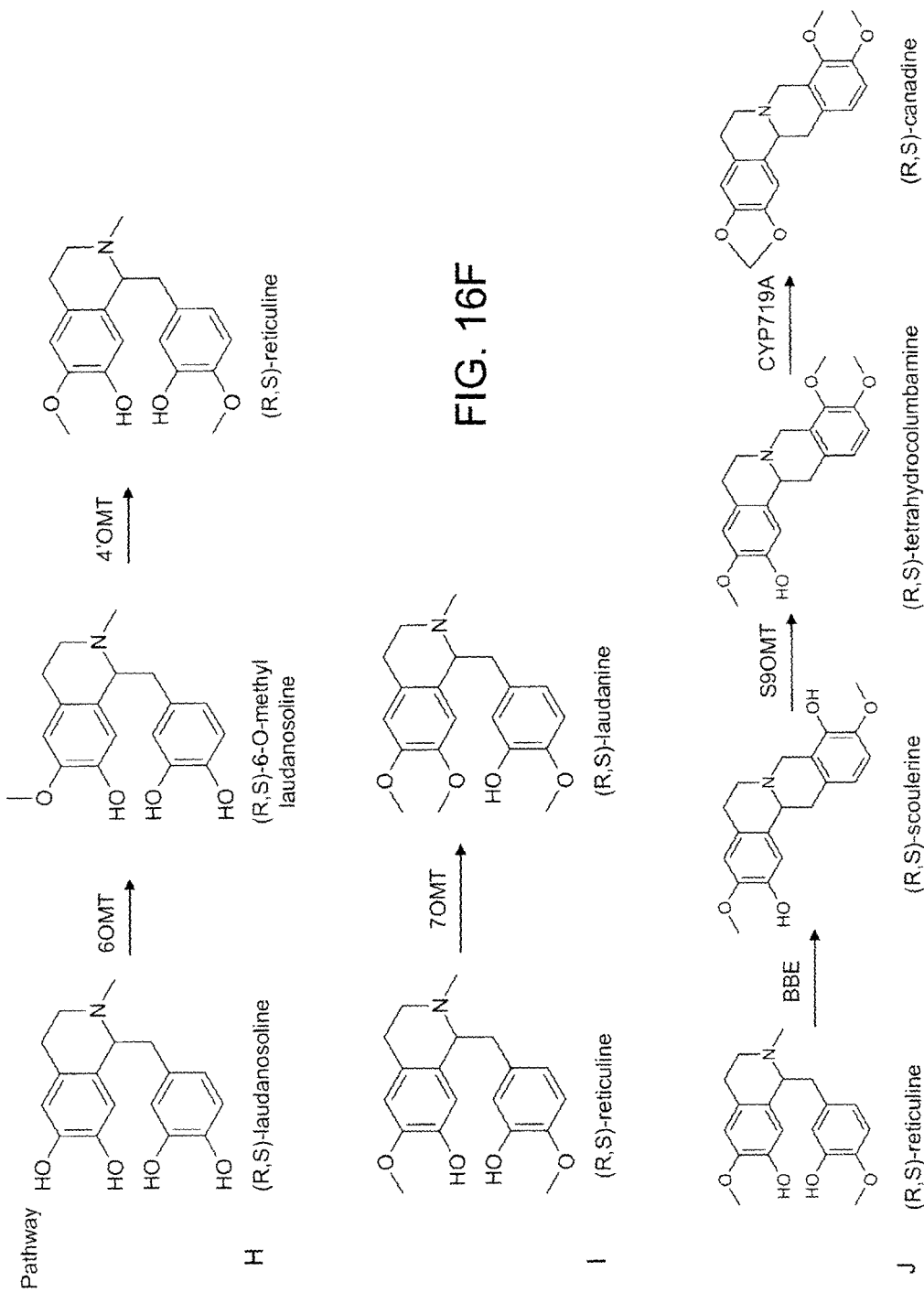
Figure 16G:
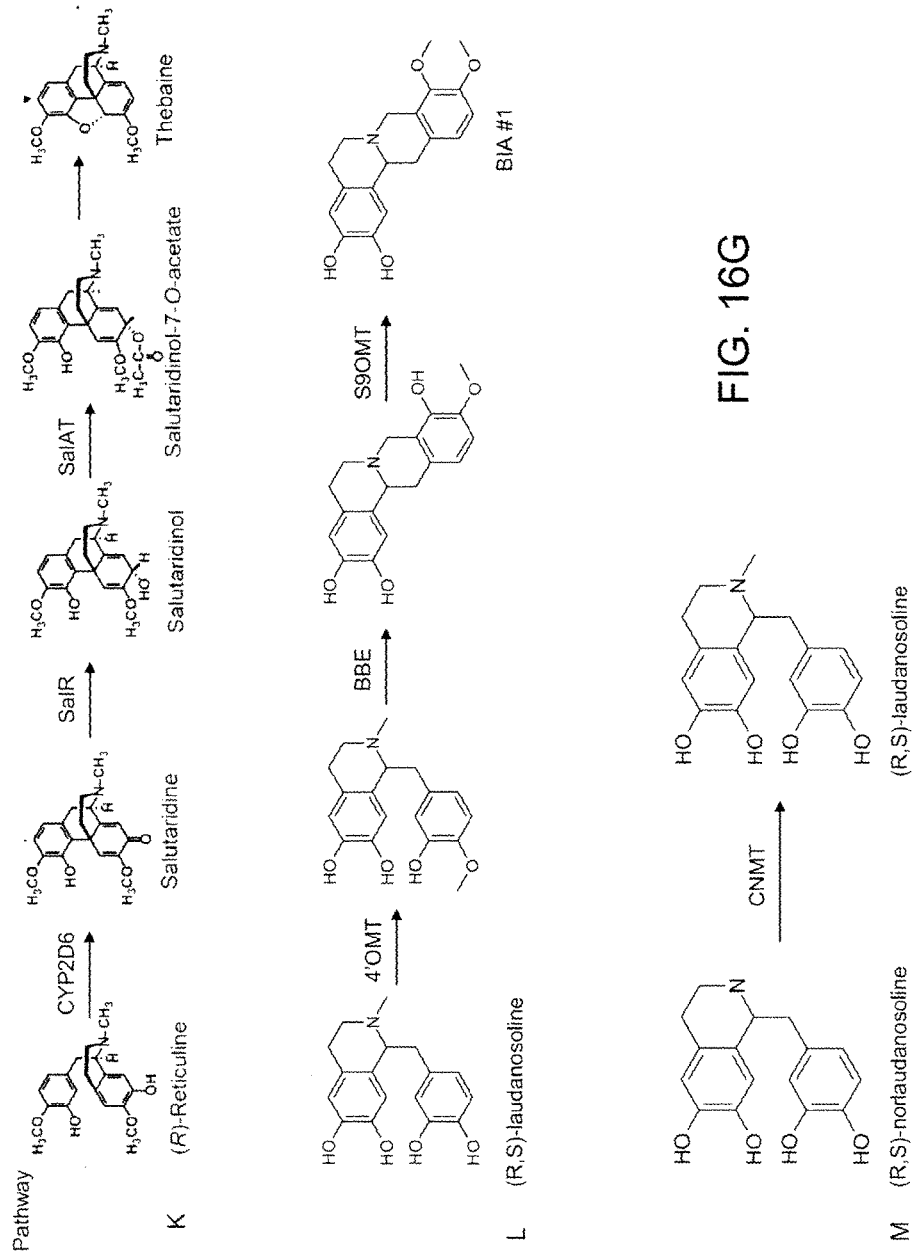
Figure 16H:
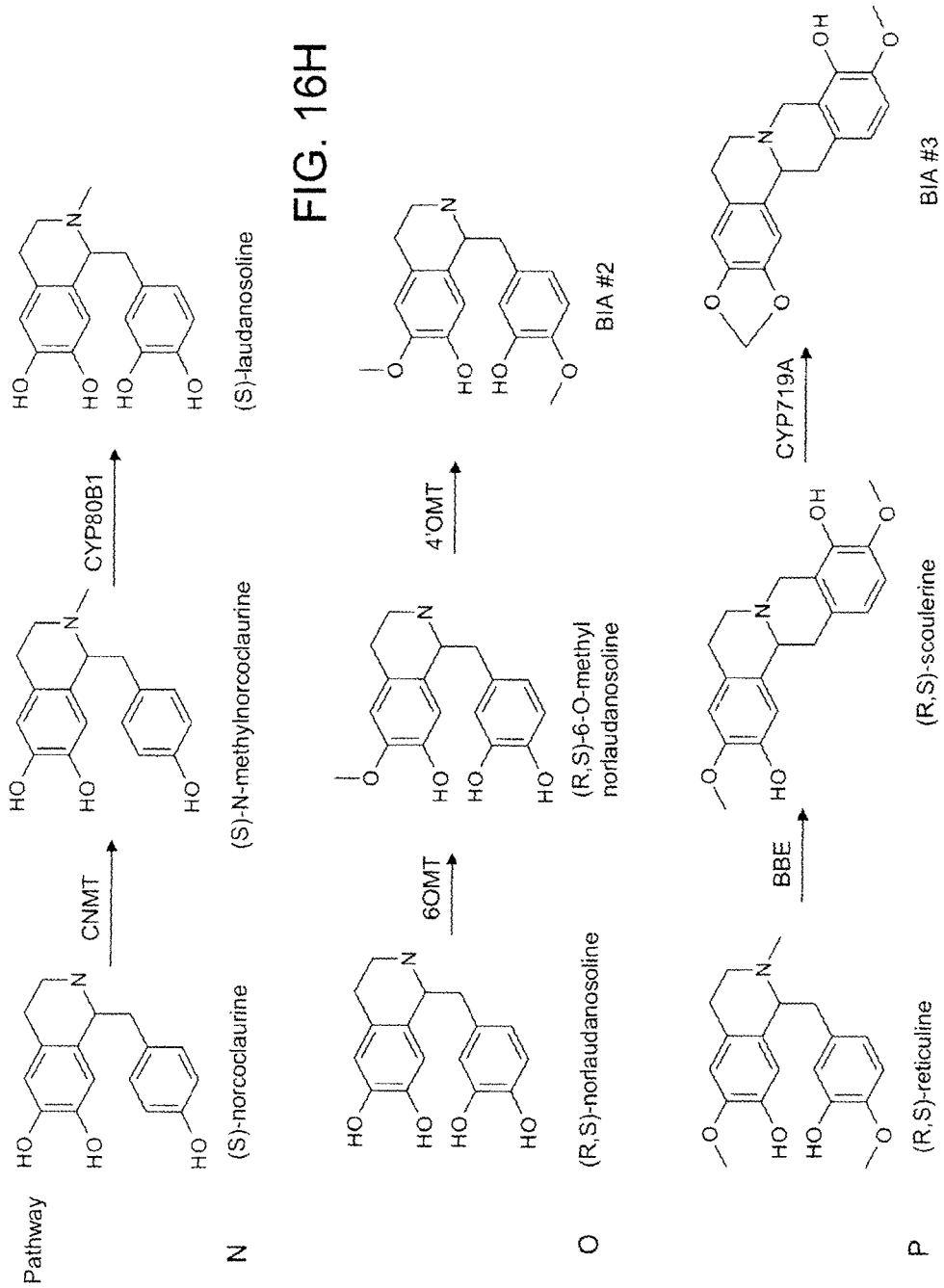
Figure 16I:
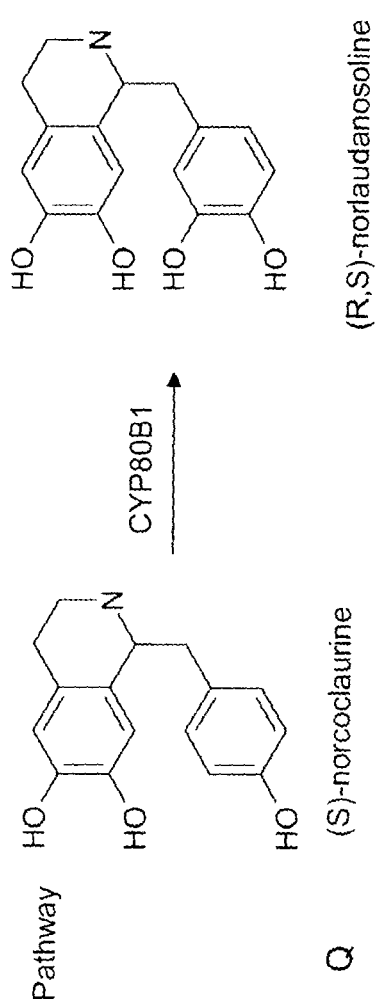
Figure 16J:
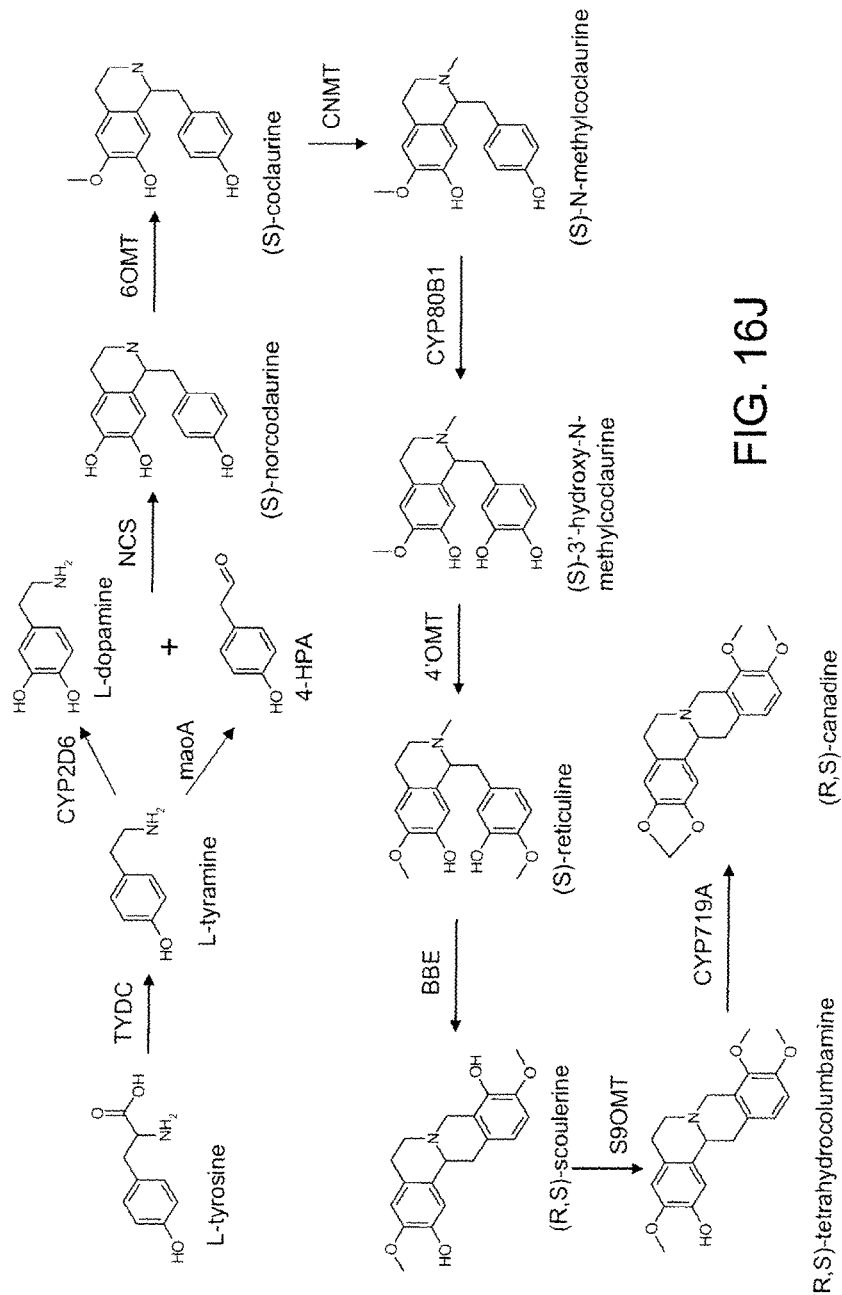

The present invention relates to compositions and methods for producing benzylisoquinoline alkaloids (BIAS). In particular, the invention relates to host cells that have been genetically engineered to express recombinant and/or have altered expression of endogenous enzymes involved in the biosynthesis of BIAs and their intermediates and derivatives.

In one embodiment, the cells of the present invention are non-plant cells. In a more particular embodiment, the cells are insect cells, mammalian cells, bacterial cells or yeast cells. Representative examples of appropriate hosts include, but are not limited to, bacterial cells, such as *Bacillus subtilis, Escherichia coli, Streptomyces* and *Salmonella typhimurium* cells and insect cells such as *Drosophila* S2 and *Spodoptera* Sf9 cells. In one specific embodiment, the cells are yeast cells or *E. coli* cells. In a more specific embodiment, the yeast cells can be of the species *Saccharomyces cerevisiae* (*S. cerevisiae*). Yeast is also an ideal host cell because cytochrome P450 proteins, which are involved in certain steps in the synthetic pathways, are able to fold properly into the endoplasmic reticulum membrane so that activity is maintained, as opposed to bacterial cells which lack such intracellular compartments. Examples of yeast strains that can be used in the invention include, but are not limited to, S288C, W303, D273-10B, X2180, A364A, Σ1278B, AB972, SK1 and FL100. In specific examples, the yeast strain is any of S288C (MATα; SUC2 mal mel gal2 CUP1 flo1 flo8-1 haply, BY4741 (MATa; his3Δ1; leu2Δ0; met15Δ0; ura3Δ0), BY4742 (MATa; his3Δ1; leu2Δ0; lys2Δ0; ura3Δ0), BY4743 (MATa/MATα; his3Δ1/his3Δ1; leu2Δ0/leu2Δ0; men 5Δ0/MET15; LYS2/lys2Δ0; ura3Δ0/ura3Δ0), and WAT11 or W(R), derivatives of the W303-B strain (MATa; ade2-1; his3-11, -15; leu2-3,-112; ura3-1; canR; cyr+) which express the *Arabidopsis thaliana* NADPH-P450 reductase ATR1 and the yeast NADPH-P450 reductase CPR1, respectively. In another specific embodiment, the particular strain of yeast cell is W303α (MATα; his3-11,15 trp1-1 leu2-3 ura3-1 ade2-1), which is commercially available. The identity and genotype of additional examples of yeast strains can be found at EUROSCARF, available through the World Wide Web at web.uni-frankfurt.de/fb15/mikro/euroscarf/col_index.html.

Other example of cells that can serve as host cells are included, but not limited to, the strains listed in the table below.

TABLE I

| CSY | EUROSCARF/Open Biosystems Accession # | ORF deleted | Gene | Strain | Background |
|---|---|---|---|---|---|
| 3 | n/a | wild type | | | W303; Mat α; his3-11, 15 trp1-1 leu2-3 ura3-1 ade2-1 |
| 142 | n/a | YER073w/YPL061w | ALD5/ALD6 | | W303; Mat α; his3-11, 15 trp1-1 leu2-3 ura3-1 ade2-1 |
| 152 | Y10753 | YMR170c | ALD2 | | BY4742; Mat α; his3Δ1; leu2Δ0; lys2Δ0; ura3Δ0; |
| 153 | Y10752 | YMR169c | ALD3 | | BY4742; Mat α; his3Δ1; leu2Δ0; lys2Δ0; ura3Δ0; |
| 154 | Y11671 | YOR374w | ALD4 | | BY4742; Mat α; his3Δ1; leu2Δ0; lys2Δ0; ura3Δ0; |
| 155 | Y10213 | YER073w | ALD5 | | BY4742; Mat α; his3Δ1; leu2Δ0; lys2Δ0; ura3Δ0; |
| 156 | Y12767 | YPL061w | ALD6 | | BY4742; Mat α; his3Δ1; leu2Δ0; lys2Δ0; ura3Δ0; |
| 157 | Y16510 | YML110c | COQ5 | | BY4742; Mat α; his3Δ1; leu2Δ0; lys2Δ0; ura3Δ0; |
| 158 | Y16246 | YOL096c | COQ3 | | BY4742; Mat α; his3Δ1; leu2Δ0; lys2Δ0; ura3Δ0; |
| 159 | Y13675 | YDR316w | OMS1 | | BY4742; Mat α; his3Δ1; leu2Δ0; lys2Δ0; ura3Δ0; |
| 160 | 30701B | YGR001c | | CVDM003-01A | BY4742; Mat α; his3Δ1; leu2Δ0; lys2Δ0; ura3Δ0; |
| 161 | Y11457 | YIL064w | | | BY4742; Mat α; his3Δ1; leu2Δ0; lys2Δ0; ura3Δ0; |
| 162 | Y15719 | YBR271w | | | BY4742; Mat α; his3Δ1; leu2Δ0; lys2Δ0; ura3Δ0; |
| 163 | B0006B | YJR129c | | CEN.EN2-1B | BY4742; Mat α; his3Δ1; leu2Δ0; lys2Δ0; ura3Δ0; |
| 164 | B0199B | YNL024c | | CEN.HE27-2C | BY4742; Mat α; his3Δ1; leu2Δ0; lys2Δ0; ura3Δ0; |
| 165 | Y12984 | YNL092w | | | BY4742; Mat α; his3Δ1; leu2Δ0; lys2Δ0; ura3Δ0; |
| 166 | Y12811 | YPL017c | | | BY4742; Mat α; his3Δ1; leu2Δ0; lys2Δ0; ura3Δ0; |
| 167 | Y12903 | YHR209w | | | BY4742; Mat α; his3Δ1; leu2Δ0; lys2Δ0; ura3Δ0; |
| 417 | 16236 | YOL086C | ADH1 | | BY4742; Mat α; his3Δ1; leu2Δ0; lys2Δ0; ura3Δ0; |
| 418 | 10891 | YMR303C | ADH2 | | BY4742; Mat α; his3Δ1; leu2Δ0; lys2Δ0; ura3Δ0; |
| 419 | 16217 | YMR083W | ADH3 | | BY4742; Mat α; his3Δ1; leu2Δ0; lys2Δ0; ura3Δ0; |
| 420 | 14623 | YGL256W | ADH4 | | BY4742; Mat α; his3Δ1; leu2Δ0; lys2Δ0; ura3Δ0; |
| 421 | 13284 | YBR145W | ADH5 | | BY4742; Mat α; his3Δ1; leu2Δ0; lys2Δ0; ura3Δ0; |
| 422 | 16460 | YMR318C | ADH6 | | BY4742; Mat α; his3Δ1; leu2Δ0; lys2Δ0; ura3Δ0; |
| 423 | 15821 | YCR105W | ADH7 | | BY4742; Mat α; his3Δ1; leu2Δ0; lys2Δ0; ura3Δ0; |
| 151 | Y10000 | wild type | | BY4742 | MATα; his3Δ1; leu2Δ0; lys2Δ0; ura3Δ0 |

The cells can be in any environment, provided the cells are able to express functional heterologous enzymes. In particular, the cells can be used in either in vitro or in vivo experiments. To be clear, in vitro, as used in the present invention, simply means outside of a living cell, regardless of the location of the cell. The term in vivo, on the other hand, indicates inside a cell, regardless of the location of the cell. In one embodiment, the cells are cultured under conditions that are conducive to enzyme expression and with appropriate substrates available to allow production of BIAs in vivo. Alternatively, the functional enzymes can be extracted from the host for production of BIAs under in vitro conditions. In another embodiment, the host cells can be placed back into a multicellular host organism. The host cells can be in any phase of growth, such as, but not limited to, stationary phase and log-growth phase, etc. In addition, the cultures themselves may be continuous cultures or they may be batch cultures.

The cell culture conditions for a particular cell type are well-known in the art and need not be repeated herein. In one particular embodiment, the host cells that comprise the various heterologous coding sequences can be cultured under standard or readily optimized conditions, with standard cell culture media and supplements. As one example, standard growth media when selective pressure for plasmid maintenance is not required may contain 20 g/L yeast extract, 10 g/L peptone, and 20 g/L dextrose (YPD). Host cells containing plasmids can be grown in synthetic complete (SC) media containing 1.7 g/L yeast nitrogen base, 5 g/L ammonium sulfate, and 20 g/L dextrose supplemented with the appropriate amino acids required for growth and selection. Alternative carbon sources which may be useful for inducible enzyme expression include sucrose, raffinose, and galactose. Cells can be grown at 30° C. with shaking at 200 rpm, typically in test tubes or flasks in volumes ranging from 1-1000 mL, or larger, in the laboratory. Culture volumes can also be scaled up for growth in larger fermentation vessels, for example, as part of an industrial process.

The term "host cells," as used in the present invention, are cells that harbor the heterologous coding sequences of the present invention. The heterologous coding sequences could be integrated stably into the genome of the host cells, or the heterologous coding sequences can be transiently inserted into the host cell. As used herein, the term "heterologous coding sequence" is used to indicate any polynucleotide that codes for, or ultimately codes for, a peptide or protein or its equivalent amino acid sequence, e.g., an enzyme, that is not normally present in the host organism and can be expressed in the host cell under proper conditions. As such, "heterologous coding sequences" includes additional copies of coding sequences that are normally present in the host cell, such that the cell is expressing additional copies of a coding sequence that are not normally present in the cells. The heterologous coding sequences can be RNA or any type thereof, e.g., mRNA, DNA or any type thereof, e.g., cDNA, or a hybrid of RNA/DNA. Examples of coding sequences include, but are not limited to, full-length transcription units that comprise such features as the coding sequence, introns, promoter regions, 3'-UTRs and enhancer regions.

"Heterologous coding sequences" also includes the coding portion of the peptide or enzyme, i.e., the cDNA or mRNA sequence, of the peptide or enzyme, as well as the coding portion of the full-length transcriptional unit, i.e., the gene comprising introns and exons, as well as "codon optimized" sequences, truncated sequences or other forms of altered sequences that code for the enzyme or code for its equivalent amino acid sequence, provided that the equivalent amino acid sequence produces a functional protein. Such equivalent amino acid sequences can have a deletion of one or more amino acids, with the deletion being N-terminal, C-terminal or internal. Truncated forms are envisioned as long as they have the catalytic capability indicated herein. Fusions of two or more enzymes are also envisioned to facilitate the transfer of metabolites in the pathway, provided again that catalytic activities are maintained.

Operable fragments, mutants or truncated forms may be identified by modeling and/or screening. This is made possible by deletion of, for example, N-terminal, C-terminal or internal regions of the protein in a step-wise fashion, followed by analysis of the resulting derivative with regard to its activity for the desired reaction compared to the original sequence. If the derivative in question operates in this capacity, it is considered to constitute an equivalent derivative of the enzyme proper.

Codon optimization is a well-known technique for optimizing the expression of heterologous polynucleotides in host cells and is reviewed in Gustafsson, C. et al., *Trends Biotechnol*, 22:346-353 (2004), which is incorporated by reference in its entirety.

The present invention also relates to heterologous coding sequences that code for amino acid sequences that are equivalent to the native amino acid sequences for the various enzymes. An amino acid sequence that is "equivalent" is defined as an amino acid sequence that is not identical to the specific amino acid sequence, but rather contains at least some amino acid changes (deletions, substitutions, inversions, insertions, etc.) that do not essentially affect the biological activity of the protein as compared to a similar activity of the specific amino acid sequence, when used for a desired purpose. The biological activity refers to, in the example of a decarboxylase, its catalytic activity. Equivalent sequences are also meant to include those which have been engineered and/or evolved to have properties different from the original amino acid sequence. Examples of mutable properties include catalytic activity, substrate specificity, selectivity, stability, solubility, localization, etc. In specific embodiments, an "equivalent" amino acid sequence contains at least 80%-99% identity at the amino acid level to the specific amino acid sequence, in particular at least about 85%, 86%, 87%, 88%, 89%, 90%, 91%, 92%, 93%, 94% and more in particular, at least 95%, 96%, 97%, 98% and 99% identity, at the amino acid level. In some cases, the amino acid sequence may be identical but the DNA sequence is altered such as to optimize codon usage for the host organism, for example.

The host cells may also be modified to possess one or more genetic alterations to accommodate the heterologous coding sequences. Alterations of the native host genome include, but are not limited to, modifying the genome to reduce or ablate expression of a specific enzyme that may interfere with the desired pathway. The presence of such native enzymes may rapidly convert one of the intermediates or final products of the pathway into a metabolite or other compound that is not usable in the desired pathway. Thus, if the activity of the native enzyme were reduced or altogether absent, the produced intermediates would be more readily available for incorporation into the desired product. For example, if the host cell is a yeast cell and the desired pathway produces 4-HPA from tyrosine, or a downstream metabolite thereof, it may be beneficial to reduce or ablate expression of the native endogenous alcohol and/or aldehyde dehydrogenase enzymes, which could convert the desired final product (4-HPA) into tyrosol or 4-hydroxyphenylacetic acid, respectively. Genetic alterations may also include modifying the promoters of endogenous genes to increase expression and/or introducing additional copies of endogenous genes. Examples of this include the construction/use of strains which overexpress the endogenous yeast NADPH-P450 reductase CPR1 to increase activity of heterologous P450 enzymes. In addition, endogenous enzymes such as ARO8, 9, and 10, which are directly involved in the synthesis of intermediate metabolites, may also be overexpressed.

The heterologous coding sequences of the present invention are sequences that encode enzymes, either wild-type or equivalent sequences, that are normally responsible for the production of BIAs in plants. The enzymes for which the heterologous sequences will code can be any of the enzymes in the BIA pathway, and can be from any known source. For example, Norcoclaurine synthase (NCS; EC 4.2.1.78) is found in at least *Thalictrum flavum*, *Papaver somniferum*, and *Coptis japonica* and is known to catalyze the condensation reaction of dopamine and 4-hydroxyphenylacetaldehyde (4-HPA) to form the trihydroxylated alkaloid (S)-norcoclaurine, which is widely accepted as the first "committed" step in the production of BIAs in plants. The choice and number of enzymes encoded by the heterologous coding sequences for the particular synthetic pathway should be chosen based upon the desired product. For example, the host cells of the present invention may comprise at least 1, 2, 3, 4, 5, 6, 7, 8, 9, 10, 11, 12, 13, 14, 15 or more heterologous coding sequences.

With regard to the heterologous coding sequences, the sequences are as reported in GENBANK unless otherwise noted. For example, the codon-optimized CYP2D6 sequence is included for reference along with the human monoamine oxidase A sequence with the first 10 amino acids optimized to facilitate translation initiation and proper folding in yeast.

A non-exhaustive list of enzymes that are contemplated in the present invention is shown in the table below. The host cells of the present invention may comprise any combination of the listed enzymes, from any source. Unless otherwise indicated, Accession numbers in Table I refer to GenBank. Some accession numbers refer to the *Saccharomyces* genome database (SGD) which is available on the worldwide web at www.yeastgenome.org.

TABLE II

| Enzyme Name | Abbrev. | Example Source Organism (Accession #) | Reference | Catalyzed Reactions |
|---|---|---|---|---|
| L-tyrosine/dopa decarboxylase 1 | TYDC1 | *P. somniferum* U08597 *T. flavum* AF314150 | Facchini, P. J. and De Luca, V. *J. Biol. Chem.* 269 (43), 26684-26690 (1994). PUBMED 7929401 | L-tyrosine→L-tyramine, L-dopa→L-dopamine |
| L-tyrosine/dopa decarboxylase 2 | TYDC2 | *P. somniferum* U08598 *V. vinifera* AM429650 | Facchini, P. J. and De Luca, V. *J. Biol. Chem.* 269 (43), 26684-26690 (1994). PUBMED 7929401 | L-tyrosine→L-tyramine, L-dopa→L-dopamine |

TABLE II-continued

| Enzyme Name | Abbrev. | Example Source Organism (Accession #) | Reference | Catalyzed Reactions |
|---|---|---|---|---|
| Cytochrome P450 2D6 | CYP2D6 | *H. sapiens* NM000106 *S. cerevisiae* codon-optimized | Hiroi, T, Imaoka, S, and Funae, Y. *Biochem Biophys Res Commun.* 1998 Aug. 28; 249(3): 838-43. PUBMED 9731223 Zhu, W et. Al. *The Journal of Immunology.* Vol. 175, pp. 7357-7362 (2005). | L-tyramine→L-dopamine (R)-reticuline→(R)-salutaridine codeine→morphine |
| NADPH p450 reductase | CPR1 | *S. cerevisiae* SGDID: S000001084 | Turi, T G and Loper, J C. *J Biol Chem.* 1992 Jan. 25; 267(3): 2046-56. PUBMED 1730736 | L-tyramine-→L-dopamine (R)-reticuline→(R)-salutaridine codeine→morphine |
| Polyphenyloxidase | PPO | *A. bisporus* X85112, AJ223816 | Wichers, H J et. Al. *Appl. Microbiol. Biotechnol.* (2003) 61: 336-341. | L-tyrosine→L-dopa |
| Tyrosine hydroxylase | TyrH | *R. norvegicus* NM 012740 | Grima, B., Lamouroux, A., Blanot, F., Biguet, N. F. and Mallet, J. *Proc. Natl. Acad. Sci. U.S.A.* 82 (2), 617-621 (1985). PUBMED 2857492 | L-tyrosine→L-dopa |
| Tyrosine hydroxylase | TH2 | *H. sapiens* NM 000240 | Grima, B., Lamouroux, A., Boni, C., Julien, J. F., Javoy-Agid, F. and Mallet, J. *Nature* 326 (6114), 707-711 (1987). PUBMED 2882428 | L-tyrosine→L-dopa |
| GTPcyclohydrolase I | GTPCH1 | *H. sapiens* NM 00161 | Leff, S E et. al. *Experimental Neurology* 151, 249-64 (1998). | Produces $BH_4$ cofactor for tyrosine hydroxylase reaction L-tyrosine→L-dopa |
| Monoamine oxidase A | MaoA | *H. sapiens* J03792 | Bach, W J et. al. *Proc. Natl. Acad Sci. USA.* Vol. 85, pp. 4934-4938, July 1988. | L-tyramine→4-HPA |
| Monoamine oxidase | maoA | *E. coli* D2367 | Azakami, H et. al. *J. Ferment. Bioeng.* 77, 315-319, 1994. | L-tyramine→4-HPA |
| Tyramine oxidase | tynA | *K. aerogenes* AB200269 | Cooper, R A. *FEMS Microbiol Lett.* 1997 Jan. 1; 146(1): 85-9. PUBMED 8997710 | L-tyramine→4-HPA |
| Aromatic amino acid transaminase | ARO8 | *S. cerevisiae* SGDID: S000003170 | Iraqui, I et. al. Mol. Gen. Genet. (1998) 257: 238-248. | L-tyrosine→4-hydroxyphenylpyruvate |
| Aromatic amino acid transaminase | ARO9 | *S. cerevisiae* SGDID: S000001179 | Iraqui, I et. al. Mol. Gen. Genet. (1998) 257: 238-248. | L-tyrosine→4-hydroxyphenylpyruvate |
| Phenylpyruvate decarboxylase | ARO10 | *S. cerevisiae* SGDID: S000002788 | Vuralhan, Z. et. al. *Appl. And Environ. Microbiol.* Vol. 71, No. 6, p. 3276-3284. | 4-hydroxyphenyl-pyruvate→4-HPA |
| Norcoclaurine synthase | NCS | *T. flavum*, AY376412 *P. somniferum* AY860500, AY860501 | Samanani, N, Liscombe, D K, and Facchini, P. *The Plant Journal* (2004) 40, 302-313. | L-dopamine + 4-HPA→ (S)-norcoclaurine |
| Norcoclaurine 6-O-methyltransferase | 6OMT | *T. flavum* AY61057 *P. somniferum* AY268894 | Ounaroon, A. et. al. *The Plant Journal* (2003) 36, 808-819. | (S)-norcoclaurine→ (S)-coclaurine norlaudanosoline→6-O-methyl norlaudanosoline laudanosoline→6-O-methyl laudanosoline |
| Coclaurine-N-methyltransferase | CNMT | *T. flavum* AY610508 | Choi, Kum-Boo et. al. *J. Biol. Chem.* | coclaurine→ N-methylcoclaurine, |

TABLE II-continued

| Enzyme Name | Abbrev. | Example Source Organism (Accession #) | Reference | Catalyzed Reactions |
|---|---|---|---|---|
| | | P. somniferum AY217336 | Vol. 277, No. 1, pp. 830-835, 2002. | laudanosoline→ N-methyl laudanosoline |
| Cytochrome P450 80B1 | CYP80B1 | P. somniferum AF191772 | Pauli, H H and Kutchan, T M. Plant J. 1998 March; 13(6): 793-801. | (S)-N-methylcoclaurine→ (S)-3'-hydroxy-N-methylcoclaurine |
| 4'-O-methyltransferase | 4'OMT | T. flavum AY610510 P. somniferum AY217333, AY217334 | Morishige, T. et. al. J. Biol. Chem. Vol. 275, No. 30, pp. 23398-23405, 2000. | 3'-hydroxy-N-methylcoclaurine→ reticuline norlaudanosoline→4'-O-methyl norlaudanosoline laudanosoline→4'-O-methyl laudanosoline |
| Berberine bridge enzyme | BBE | P. somniferum AF025430 | Facchini, P. J., Penzes, C., Johnson, A. G. and Bull, D. Plant Physiol. 112 (4), 1669-1677 (1996). PUBMED 8972604 | (S)-reticuline→ (S)-scoulerine |
| Reticuline 7-O-methyltransferase | 7OMT | P. somniferum AY268893 | Ounaroon, A. et. al. The Plant Journal (2003) 36, 808-819. | reticuline→ laudanine |
| Scoulerine 9-O-methyltransferase | S9OMT | T. flavum AY610512 | Samanani, N., Park, S. U. and Facchini, P. J. Plant Cell 17 (3), 915-926 (2005). PUBMED 15722473 | (S)-scoulerine→ (S)-tetrahydrocolumbamine |
| Canadine synthase | CYP719A | T. flavum AY610513 | Samanani, N., Park, S. U. and Facchini, P. J. Plant Cell 17 (3), 915-926 (2005). PUBMED 15722473 Ikezawa, N. et. al. J. Biol. Chem. Vol. 278, No. 40, pp. 38557-38565, 2003. | (S)tetrahydrocolumbamine→ (S)-canadine |
| NADPH P450 reductase | ATR1 | A. thaliana NM 118585 | Louërat-Oriou B, Perret A, Pompon D. Eur J Biochem. 1998 Dec. 15; 258(3): 1040-9. | Reductase partner for cytochrome P450s Ex. (S)tetrahydro-columbamine→ (S)-canadine |
| Salutaridine reductase | SalR | P. somniferum DQ316261 | Ziegler, J. et. al. Plant J. 48 (2), 177-192 (2006) | salutaridine→salutaridinol |
| Salutaridinol 7-O-acetyltransferase | SalAT | P. somniferum AF339913 | Grothe, T., Lenz, R. and Kutchan, T. M. J. Biol. Chem. 276 (33), 30717-30723 (2001). PUBMED 11404355 | salutaridinol→salutaridinol-7-O-acetate→thebaine |
| Codeine reductase | COR | P. somniferum AF108432 | Unterlinner, B., Lenz, R. and Kutchan, T. M. Plant J. 18 (5), 465-475 (1999). PUBMED 1041769 | codeinone→codeine |
| Berbamunine synthase | CYP80A1 | B. stolonifera U09610 | Kraus, P F and Kutchan, T M. Proc Natl Acad Sci USA. 1995 Mar. 14; 92(6): 2071-5. | 2 (R)-N-methylcoclaurine→guattegaumerine (R)-N-methlcoclaurine + (S)-N-methylcoclaurine→berbamunine |

In one specific embodiment, the present invention relates to host cells that produce 4-Hydroxyphenylacetaldehyde (4-HPA) from tyrosine. For example, the host cells that produce 4-HPA from tyrosine comprise at least two heterologous coding sequences, wherein each of the heterologous coding sequences encodes a separate enzyme that is involved in the biosynthetic pathway that converts tyrosine to 4-HPA. In a more specific embodiment, the host cells that produce 4-HPA from tyrosine comprise L-tyrosine/dopa decarboxylase (TYDC, P. somniferum) and one of monoamine oxidase (maoA, *E. coli* or *Homo sapiens*) or Tyramine oxidase (tyn A, *Klebsiella aerogenes*). In another specific embodiment, the host cells that produce 4-HPA from tyrosine comprise Aromatic amino acid transaminase (ARO8/ARO9, *S. cerevisiae*) and Phenylpyruvate decarboxylase (ARO10, *S. cerevisiae*).

In another specific embodiment, the present invention relates to host cells that produce dopamine from tyrosine. For example, the host cells that produce dopamine comprise at least two heterologous coding sequences, wherein each of the heterologous coding sequences encodes a separate enzyme that is involved in the biosynthetic pathway that converts tyrosine to dopamine. In a more specific embodiment, the host cells that produce dopamine from tyrosine comprise a Tyrosine/dopa decarboxylase (TYDC, *P. somniferum*) and one of Cytochrome P450 2D6 (CYP2D6, *H. sapiens*) or Codon-Optimized Cytochrome P450 2D6 (CYP2D6, *S. cerevisiae*). To improve of the activity of CYP2D6, additional copies of the yeast NADPH-P450 reductase (yCPR1) may be expressed either from the chromosome or a plasmid. In another specific embodiment, the host cells that produce dopamine from tyrosine comprise a Tyrosine hydroxylase (PPO *Agaricus bisporus*; TH2, *H. sapiens*; TyrH, *Rattus norvegicus*) and Tyrosine/dopa decarboxylase (TYDC, *P. somniferum*).

In another specific embodiment, the present invention relates to host cells that convert tyrosine into norcoclaurine. Regardless of the source of the tyrosine starting material, the host cells of the present invention that produce norcoclaurine comprise at least three heterologous coding sequences, wherein each of the heterologous coding sequences encodes a separate enzyme, or its equivalent, that is involved in the biosynthetic pathway that converts tyrosine to norcoclaurine. In one specific embodiment, the host cells that produce norcoclaurine from tyrosine comprise the L-tyrosine/dopa decarboxylase (TYDC, *P. somniferum*), Monoamine oxidase (MaoA, *E. coli*), one of Cytochrome P450 2D6 (CYP2D6, *H. sapiens*) or Codon-Optimized Cytochrome P450 2D6 (CYP2D6, *S. cerevisiae*), and NCS (*T. flavum* or *P. somniferum*) coding sequences. To improve the activity of CYP2D6, additional copies of the endogenous yeast P450 NADPH reductase (yCPR1) may be expressed either from the chromosome or a plasmid. Of course, the embodiment above may further comprise additional heterologous coding sequences that will continue the synthetic pathway to create at least one additional metabolite. For example, the presence of the heterologous coding sequence that codes for Norcoclaurine 6-O-methyltransferase (6OMT, *T. flavum*, *P. somniferum*) will further metabolize norcoclaurine into coclaurine. Other pathways to/from norcoclaurine are depicted herein.

The embodiment above can serve as the basis of additional embodiments. For example, embodiments comprising TYDC, CYP2D6, maoA, NCS, 6OMT may further comprise the Coclaurine-N-methyltransferase (CNMT, *T. flavum*, *P. somniferum*) heterologous coding sequence, the embodiments of which may further comprise the Cytochrome P450 80B1 (CYP80B1, *P. somniferum*) heterologous coding sequence, the embodiments of which may further comprise the 4'O-methyltransferase (4'OMT, *T. flavum*, *P. somniferum*) heterologous coding sequence, the embodiments of which may further comprise Berberine bridge enzyme (BBE, *P. somniferum*), etc. The embodiments in which the host cell comprises TYDC, CYP2D6, maoA, NCS, 6OMT and CNMT will generate N-methylcoclaurine ultimately from tyrosine. The embodiments in which the host cell comprises TYDC, CYP2D6, maoA, NCS, 6OMT, CNMT and CYP80B1 will generate 3'-Hydroxy-N-methylcoclaurine ultimately from tyrosine. The embodiments in which the host cell comprises TYDC, CYP2D6, maoA, NCS, 6OMT, CNMT CYP80B1 and 4'OMT will generate reticuline ultimately from tyrosine. The embodiments in which the host cell comprises TYDC, CYP2D6, maoA, NCS, 6OMT, CNMT CYP80B1, 4'OMT and BBE will generate scoulerine ultimately from tyrosine. All strains containing either CYP2D6 and/or CYP80B1 will likely require overexpression of CPR1 and/or ATR1 NADPH-P450 reductases for optimal activity.

Of course, the desired pathways need not start with tyrosine. For example, the synthetic pathways generated in the host cells may start with laudanosoline, methyl laudanosoline, norlaudanosoline, methyl norlaudanosoline, or another compound that may or may not be normally present in the endogenous BIA pathway. Thus, the starting material may be non-naturally occurring or the starting material may be naturally occurring. Additional examples of starting material include, but are not limited to, tyramine, dopamine, 4-HPA, 4-HPPA, norcoclaurine, coclaurine, N-methylcoclaurine, 3'-hydroxy-N-methylcoclaurine, reticuline, scoulerine, tetrahydrocolumbamine, canadine, laudanine, sanguinarine, morphine, codeine, codeinone and dimethyl tetrahydoisoquinoline, e.g., 6,7-dimethyl-1-2-3-4-tetrahydroisoquinoline. Other compounds may also be used as the starting material in the desired synthetic pathway and one of skill in the art would recognize the necessary starting material, based upon the synthetic pathway present in the host cell. The source of the starting material may be from the host cell itself, e.g., tyrosine, or the starting material may be added or supplemented to the host cell from an outside source. For example, if the host cells are growing in liquid culture (an in vivo environment), the cell media may be supplemented with the starting material, e.g., tyrosine or norlaudanosoline, which is transported into the cells and converted into the desired products.

In one embodiment, the host cells of the claimed invention convert norlaudanosoline into reticuline. The norlaudanosoline may be generated through a normal or synthetic pathway in the same or different host cell, or the norlaudanosoline may be fed to the cells from the outside. In this particular embodiment, the host cells comprise 6OMT, CNMT and 4'OMT. This embodiment can serve as the basis of additional embodiments. For example, embodiments comprising 6OMT, CNMT and 4'OMT may further comprise BBE or Reticuline 7-O-methyltransferase (7OMT, *P. somniferum*) the embodiments of which may further comprise Scoulerine 9-O-methyltransferase (S9OMT, *T. flavum*), the embodiments of which may further comprise Canadine synthase (CYP719A, *T. flavum*). The embodiments that comprise 6OMT, CNMT and 4'OMT will generate reticuline from norlaudanosoline. The embodiments that comprise 6OMT, CNMT, 4'OMT and BBE will generate scoulerine from norlaudanosoline. The embodiments that comprise 6OMT, CNMT, 4'OMT, and CYP2D6 with its reductase partner (CPR1 or ATR1) will generate salutaridine from norlaudanosoline. The embodiments that comprise 6OMT, CNMT, 4'OMT and 7OMT will generate laudanine from norlaudanosoline. The embodiments that comprise 6OMT, CNMT, 4'OMT, BBE and S9OMT will generate tetrahydrocolumbamine from norlaudanosoline. The embodiments that comprise 6OMT, CNMT, 4'OMT, BBE, S9OMT and CYP719A with its reductase partner ATR1 will generate canadine from norlaudanosoline.

The following is a non-exhaustive list of exemplary host organisms comprising heterologous coding sequences. The list is not intended to limit the scope of the invention in any way.

TABLE III

| Strain | Background | Plasmid(s) | Enzyme(s) |
|---|---|---|---|
| CSY73 | W303α | | $P_{ARO9}$::TEF, $P_{ARO10}$::TEF |
| CSY87 | W303α | pCS251 | $P_{TEF1}$-AbPPO2 |
| CSY88 | W303α | pCS251, pCS221 | $P_{TEF1}$-AbPPO2, $P_{TEF1}$-TYDC2 |
| CSY94 | W303α | pCS250, pCS283 | $P_{TEF1}$-TfNCSΔ10, $P_{TEF1}$-TYDC2, $P_{TEF1}$-maoA |
| CSY95 | W303α | | ChrIV 122460::$P_{TEF1}$-TYDC2 |
| CSY104 | CSY95 | | ChrV 1100::$P_{TEF1}$-maoA |
| CSY107 | W303α | pCS222, pCS330 | $P_{tetO7}$-yCPR1, $P_{TEF1}$-TYDC2, $P_{TEF1}$-yCYP2D6 |
| CSY116 | CSY104 | | his3::$P_{GPD}$-yCPR1 |
| CSY176 | W303α | | his3::$P_{GAL1}$-TfNCS |
| CSY177 | W303α | | his3::$P_{GAL1}$-Tf6OMT |
| CSY178 | W303α | | his3::$P_{GAL1}$-PsNCS2 |
| CSY179 | W303α | | his3::$P_{GAL1}$-Ps6OMT |
| CSY234 | CSY194 W(R) | pCS330 | $P_{TEF1}$-TYDC2, $P_{TEF1}$-yCYP2D6 |
| CSY235 | CSY194 W(R) | pCS222, pCS330 | $P_{tetO7}$-yCPR1, $P_{TEF1}$-TYDC2, $P_{TEF1}$-yCYP2D6 |
| CSY307 | W303α | pCS827, pCS830 | $P_{TEF1}$-Ps6OMT, $P_{TEF1}$-PsCNMT, $P_{TEF1}$-Ps4'OMT |
| CSY308 | W303α | pCS828, pCS830 | $P_{TEF1}$-Ps6OMT, $P_{TEF1}$-TfCNMT, $P_{TEF1}$-Ps4'OMT |
| CSY309 | W303α | pCS829, pCS830 | $P_{TEF1}$-Tf6OMT, $P_{TEF1}$-PsCNMT, $P_{TEF1}$-Ps4'OMT |
| CSY310 | W303α | pCS772, pCS830 | $P_{TEF1}$-Tf6OMT, $P_{TEF1}$-TfCNMT, $P_{TEF1}$-Ps4'OMT |
| CSY311 | W303α | pCS827, pCS831 | $P_{TEF1}$-Ps6OMT, $P_{TEF1}$-PsCNMT, $P_{TEF1}$-Tf4'OMT |
| CSY312 | W303α | pCS828, pCS831 | $P_{TEF1}$-Ps6OMT, $P_{TEF1}$-TfCNMT, $P_{TEF1}$-Tf4'OMT |
| CSY313 | W303α | pCS829, pCS831 | $P_{TEF1}$-Tf6OMT, $P_{TEF1}$-PsCNMT, $P_{TEF1}$-Tf4'OMT |
| CSY314 | W303α | pCS772, pCS831 | $P_{TEF1}$-Tf6OMT, $P_{TEF1}$-TfCNMT, $P_{TEF1}$-Tf4'OMT |
| CSY288 | W303α | | his3::$P_{TEF1}$-Ps6OMT, leu2::$P_{TEF1}$-PsCNMT, ura3::$P_{TEF1}$-Ps4'OMT |
| CSY334 | W303α | | his3::$P_{TEF1}$-Ps6OMT, leu2::$P_{TEF1}$-PsCNMT, ura3::$P_{TEF1}$-Tf4'OMT |
| CSY316 | W303α | | his3::$P_{GAL1}$-Ps6OMT-loxP-KanR, leu2::$P_{TEF1}$-PsCNMT, ura3::$P_{TEF1}$-Ps4'OMT |
| CSY317 | W303α | | his3::$P_{TEF1}$-Ps6OMT, leu2::$P_{GAL1}$-PsCNMT-loxP-URA3, ura3::$P_{TEF1}$-Ps4'OMT |
| CSY318 | W303α | | his3::$P_{TEF1}$-Ps6OMT, leu2::$P_{TEF1}$-PsCNMT, ura3::$P_{GAL1}$-Ps4'OMT-loxP-LEU2 |
| CSY319 | W303α | | his3::$P_{TEF1}$-Ps6OMT, leu2::$P_{TEF1}$-PsCNMT, ura3::$P_{GAL1}$-Tf4'OMT-loxP-LEU2 |
| CSY325 | W303α | | his3::$P_{GAL1}$-Ps6OMT-loxP-KanR, leu2::$P_{TEF1}$-PsCNMT, ura3::$P_{TEF1}$-Ps4'OMT, gal2::HIS3 |
| CSY326 | W303α | | his3::$P_{TEF1}$-Ps6OMT, leu2::$P_{GAL1}$-PsCNMT-loxP-URA3, ura3::$P_{TEF1}$-Ps4'OMT, gal2::HIS3 |
| CSY327 | W303α | | his3::$P_{TEF1}$-Ps6OMT, leu2::$P_{TEF1}$-PsCNMT, ura3::$P_{GAL1}$-Ps4'OMT-loxP-LEU2, gal2::HIS3 |
| CSY328 | W303α | | his3::$P_{TEF1}$-Ps6OMT, leu2::$P_{TEF1}$-PsCNMT, ura3::$P_{GAL1}$-Tf4'OMT-loxP-LEU2, gal2::HIS3 |
| CSY336 | CSY288 | pCS1018 | $P_{TEF1}$-PsBBE |
| CSY337 | CSY288 | pCS1070 | $P_{TEF1}$-PsBBE, $P_{TEF1}$-TfS9OMT |
| CSY338 | CSY334 | pCS1018 | $P_{TEF1}$-PsBBE |
| CSY339 | CSY334 | pCS1070 | $P_{TEF1}$-PsBBE, $P_{TEF1}$-TfS9OMT |
| CSY399 | CSY288 | pCS1018, pCS953, pCS1058 | $P_{TEF1}$-PsBBE, $P_{TEF1}$-TfS9OMT, $P_{TEF1}$-TfCYP719A, $P_{TEF1}$-AtATR1 |
| CSY400 | CSY334 | pCS1018, pCS953, pCS1058 | $P_{TEF1}$-PsBBE, $P_{TEF1}$-TfS9OMT, $P_{TEF1}$-TfCYP719A, $P_{TEF1}$-AtATR1 |
| CSY401 | CSY288 | pCS1163 | $P_{TEF1}$-PsR7OMT |
| CSY402 | CSY334 | pCS1163 | $P_{TEF1}$-PsR7OMT |
| CSY409 | CSY334 | | his3::$P_{TEF1}$-Ps6OMT, leu2::$P_{TEF1}$-PsCNMT, ura3::$P_{TEF1}$-Tf4'OMT, trp1::$P_{TEF1}$-AtATR1(KanR) |
| CSY410 | CSY409 | pCS1018, pCS953 | $P_{TEF1}$-PsBBE, $P_{TEF1}$-TfS9OMT, $P_{TEF1}$-TfCYP719A |
| CSY424 | CSY334 | pCS782 | $P_{TEF1}$-yCYP2D6 |
| CSY425 | CSY409 | pCS782 | $P_{TEF1}$-yCYP2D6 |
| CSY426 | CSY288 | | trp1::$P_{TEF1}$-yCPR1(KanR) |
| CSY427 | CSY426 | pCS782 | $P_{TEF1}$-yCYP2D6 |

The promoters driving expression of the heterologous coding sequences can be constitutive promoters or inducible promoters, provided that the promoters can be active in the host cells. The heterologous coding sequences may be expressed from their native promoters, or non-native promoters may be used. Although not a requirement, such promoters should be medium to high strength in the host in which they are used. Promoters may be regulated or constitutive. In one embodiment, promoters that are not glucose repressed, or repressed only mildly by the presence of glucose in the culture medium, should be used. There are numerous suitable promoters, examples of which include promoters of glycolytic genes such as the promoter of the B. subtilis tsr gene (encoding fructose biphosphate aldolase) or GAPDH promoter from yeast S. cerevisiae (coding for glyceraldehyde-phosphate dehydrogenase) (Bitter G. A., Meth. Enzymol. 152:673 684 (1987)). Other strong promoters include the ADHI promoter of baker's yeast (Ruohonen L., et al., J. Biotechnol. 39:193 203 (1995)), the phosphate-starvation induced promoters such as the PHO5 promoter of yeast (Hinnen, A., et al., in Yeast Genetic Engineering, Barr, P. J., et al. eds, Butterworths (1989), and the alkaline phosphatase promoter from B. licheniformis (Lee. J. W. K., et al., J. Gen. Microbiol. 137:1127 1133 (1991)). Some specific examples of yeast promoters include inducible promoters such as Gall-10, Gall, GalL, GalS, repressible promoter Met25, tetO, and constitutive promoters such as glyceraldehyde 3-phosphate dehydrogenase promoter (GPD), alcohol dehydrogenase promoter (ADII), translation-elongation factor-1-alpha promoter (TEF), cytochrome c-oxidase promoter (CYC1), MRP7 promoter, etc. Autonomously replicating yeast expression vectors containing promoters inducible by hormones such as glucocorticoids, steroids, and thyroid hormones are also known and include, but are not limited to, the glucorticoid responsive element (GRE) and thyroid hormone responsive element (TRE). These and other examples are described U.S. Pat. No. 7,045,290, which is incorporated by reference, including the references cited therein. Additional vectors containing constitutive or inducible promoters such as alpha factor, alcohol oxidase, and PGH may be used. Additionally any promoter/enhancer combination (as per the Eukaryotic Promoter Data Base EPDB) could also be used to drive expression of genes. Similarly, one of skill in the art can choose appropriate promoters specific to the host cell, e.g., *E. coli*. One can also use promoter selection to optimize transcript, and hence, enzyme levels to maximize production while minimizing energy resources.

Vectors useful in the present invention include vectors for use in yeast and other cells. Yeast vectors can be broken up into 4 general categories: integrative vectors (YIp), autonomously replicating high copy-number vectors (YEp), autonomously replicating low copy-number vectors (YCp) and vectors for cloning large fragments (YACs). There are myriad of yeast expression vectors that are commercially available from sources such as, but not limited to, American Type Culture Collection (ATCC, Manassas, Va., USA) and Invitrogen Corp. (Carlsbad, Calif., USA).

Alternatively, insect cells may be used as host cells. In one embodiment, the polypeptides of the invention are expressed using a baculovirus expression system (see, Luckow et al., Bio/Technology, 1988, 6, 47; BACULOVIRUS EXPRESSION VECTORS: A LABORATORY MANUAL, O'Rielly et al. (Eds.), W.H. Freeman and Company, New York, 1992; and U.S. Pat. No. 4,879,236, each of which is incorporated herein by reference in its entirety). In addition, the MAX-BAC™ complete baculovirus expression system (Invitrogen) can, for example, be used for production in insect cells.

Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin, dihydrofolate reductase (DHFR) and methotrexate. Nucleic acid encoding a selectable marker can be introduced into a host cell on the same vector as that encoding the functional enzyme, or its equivalent, or can be introduced on a separate vector. Cells stably transfected with the introduced nucleic acid can be identified by drug selection (e.g., cells that have incorporated the selectable marker gene will survive, while the other cells die).

Similarly, if the host cells are bacterial cells or animal or insect cells, there are a variety of commercially available expression vectors from which to choose. The choice of expression vector system will be apparent to one of skill in the art. One example of a yeast expression vector includes, but is not limited to, p413-TEF, p426-GPD, pCM190, pRS313, pYES2-NT/A, etc.

The choice of yeast plasmids will depend on the host. For *Z. rouxii* vectors based on the native cryptic plasmids pSRI (Toh, E. et al., *J. Bacteriol.* 151:1380-1390 (1982)), pSB1, pSB2, pSB3 or pSB4 (Toh-E et al., *J. Gen. Microbiol.* 130:2527-2534 (1984)) may be used. Plasmid pSRT303D (Jearnpipatkul, A., et al., *Mol. Gen. Genet.* 206:88-94 (1987)) is an example of useful plasmid vector for *Zygosaccharomyces* yeast.

Methods of transforming yeast for the purposes of the present invention are well known in the art. Briefly, inserting DNA into yeast can be accomplished with techniques that include but are not limited to, those using spheroplasts, treating with lithium salts and electroporation. The methods are used to insert the heterologous coding sequences into the host cells such that the host cells will functionally express the enzymes or their equivalents and convert the starting/intermediate compounds into the desired end product.

Of course, the present invention also relates to methods of producing BIAs comprising culturing the host cells under conditions suitable for protein production such that the heterologous coding sequences are expressed in the host cells and act upon the starting/intermediate molecules.

In another embodiment of the present invention the host cells may also be used for functional genomics studies in both plant and animals. For example, host cells that are able to convert a given substrate such as norlaudanosoline into reticuline or other downstream BIAs can be used to screen libraries of plant cDNA sequences to discover enzymes which act on the product molecule. Of course, the screening methods can also be applied to precursors of BIAs. The screening methods can be accomplished by cloning a cDNA library from an organism, such as a plant or any organism that produces BIAs or an intermediate thereof, e.g., dopamine; into a suitable expression vector, e.g., a yeast expression vector, and transforming the library of plasmids into the engineered host cells. The standard LiAc/SSD/PEG method can be used Single colonies can then be grown in liquid culture in the presence of substrate and the growth media or cell extract analyzed by LC-MS. New BIA molecules and the corresponding enzymes catalyzing their production can be identified by chromatogram peaks not present in strains lacking the cDNA library sequence. In vitro or other high-throughput methods can also be used if a suitable assay has been developed for a particular metabolite or byproduct, for example. An additional area of study where these engineered host cells can be employed is in the characterization of the recombinant enzymes known or suspected to be involved in these pathways. In particular, host cells expressing one or more heterologous coding sequences can be grown in the presence of various substrates and the resulting metabolites analyzed by LC-MS or other methods. Both in vivo and in vitro methods can be used in this manner to determine the substrate specificities of these enzymes and possibly discover new catalytic activities.

EXAMPLES

Example 1—Construction of Yeast Expression Vectors

Standard molecular biology methods were used to construct the yeast expression vectors. Heterologous coding sequences for the genes of interest were received as plasmids, typically suited for expression in *E. coli*. Coding sequences were either amplified by polymerase chain reaction (PCR) or excised from the vectors if restriction sites were compatible with the destination vector. Briefly, yeast shuttle vectors were constructed based on pCM185 and pCM180 which have an ampicillin resistance marker for maintenance in *E. coli*, URA and TRY selection markers, respectively, and a centromeric (ARS1/CEN4) origin of replication for yeast. To construct exemplary vectors, the TEF1 promoter was amplified from p413-TEF and the CYC1 promoter from pCM190 and assembled with the NCS coding sequence using PCR methods. Primers for each segment included suitable restriction sites both for cloning into the plasmid backbone and allowing the coding sequence to be easily replaced. This promoter-gene-terminator assembled PCR product was cloned into XhoI/BamHI sites of pCM185. Similar methods were used to make a second DNA insert containing the TEF promoter and 6OMT gene, which was then cloned into PmeI/NotI sites of the previous vector such that a CYC1 terminator for this gene was included on the plasmid backbone. Similar methods were used to construct the analogous vector with a TRP selection marker. In later constructs, the origin of replication was replaced with the 2µ origin using standard cloning procedures to allow for high copy expression in yeast. For cloning and expression of desired enzyme combinations, heterologous coding sequences were cloned into these primary vectors; restriction sites were changed using site-directed mutagenesis if necessary. To remove the second gene from these constructs, vectors were digested with MluI and self-ligated. To remove the first gene from these constructs, the vectors were digested with XhoI and either BamHI or PmeI, ends were blunted using the Klenow enzyme, and self-ligated. Alternatively, a single promoter vector can be made by cloning the gene of interest between the first promoter and second terminator. Analogous vectors with the HIS selection marker were also constructed as needed; for example, to express more than four heterologous coding sequences.

Example 2—Production of Codon-Optimized CYP2D6

The coding sequence for CYP2D6 was optimized based on codon usage in *S. cerevisiae* as well as RNA secondary structure, using commercially available service providers, such as DNA2.0 Inc. (Menlo Park, Calif., USA). There are other service providers that offer codon-optimized sequences, and some algorithms are available on the world-wide web.

The following is an example of a sequence for yeast codon-optimized CYP2D6 sequence; SalI and NotI restriction sites for cloning are underlined.

```
   1 GTCGACATGG CATTGGAAGC ACTAGTCCCT TTAGCTGTAA TTGTAGCAAT
  51 ATTCCTGTTA TTGGTAGACC TTTATGCATAG AAGACAAAGA TGGGCTGCAA
 101 GATACCCACC CGGCCCACTA CCCTTGCCAG GACTAGGTAA CCTTTTACAT
 151 GTTGATTTCC AAAATACTCC GTACTGTTTT GATCAATTGA GGAGAAGATT
 201 CGGAGATGTT TTCAGTCTGC AGTTGGCATG GACACCAGTC GTCGTTTTAA
 251 ATGGTTTGGC TGCAGTAAGA GAAGCTTTAG TTACGCATGG CGAAGATACG
 301 GCGGACAGGC CTCCTGTGCC CATTACACAG ATATTGGGTT TCGGACCTAG
 351 ATCTCAGGGT GTATTCCTTG CCCGTTACGG TCCTGCGTGG AGAGAACAGA
 401 GAAGGTTTTC TGTATCAACA CTTAGGAATT TGGGTCTAGG CAAGAAATCA
 451 TTGGAACAAT GGGTGACCGA GGAAGCCGCT TGTTTGTGCG CAGCCTTTGC
 501 TAATCATTCT GGCCGTCCTT TTAGACCTAA TGGATTACTT GATAAAGCAG
 551 TATCTAATGT GATTGCCTCC TTAACATGTG GTAGACGTTT TGAGTACGAT
 601 GACCCAAGGT TTTTGAGATT GTTAGATCTA GCACAAGAGG GATTAAAGGA
 651 AGAAATGGGT TTCTTGAGAG AGGTTTTGAA TGCTGTTCCA GTGCTATTAC
 701 ACATTCCAGC CCTAGCTGGA AAGGTCTTGA GATTTCAAAA GGCTTTCTTA
 751 ACGCAGCTTG ATGAGTTACT TACAGAGCAT AGGATGACTT GGGATCCTGC
 801 TCAACCCCCG AGAGATCTAA CCGAGGCCTT CCTGGCTGAA ATGGAAAAAG
 851 CAAAGGGTAA TCCGGAAAGT TCCTTCAATG ATGAAAACCT GAGAATTGTC
 901 GTGGCGGACT TGTTCTCTGC CGGAATGGTG ACAACGTCTA CTACTTTGGC
 951 CTGGGGACTT CTATTAATGA TTCTTCATCC AGACGTCCAG AGAAGAGTGC
1001 AACAAGAAAT AGATGATGTG ATAGGACAAG TTAGAAGGCC AGAAATGGGT
1051 GACCAGGCAC ATATGCCATA TACGACTGCT GTAATCCATG AAGTGCAACG
1101 TTTTGGGGAC ATTGTCCCCT TGGGAATGAC CCACATGACT TCTCGTGATA
1151 TTGAAGTACA AGGTTTCAGA ATACCAAAGG GAACTACGCT GATTACGAAT
```

-continued

```
1201 CTGTCTAGCG TGCTAAAAGA CGAAGCTGTC TGGGAGAAGC CATTTAGGTT

1251 TCATCCAGAA CACTTCTTAG ACGCTCAGGG TCATTTCGTA AAGCCTGAAG

1301 CATTCCTTCC GTTTAGTGCC GGACGTAGGG CGTGTTTGGG TGAACCATTA

1351 GCTAGAATGG AATTATTCCT TTTTTTTACA TCTTTATTGC AGCACTTTTC

1401 ATTTTCTGTT CCGACTGGCC AACCCAGACC TAGCCATCAT GGTGTTTTTG

1451 CTTTCCTAGT TTCTCCCTCT CCTTATGAAT TATGCGCGGT TCCCCGTTGA

1501 GCGGCCGC
```

The following is an example of human MAO A sequence optimized for expression in yeast and includes 8 nt preceding the start codon, which is underlined:

```
   1 AATTAATAAT GGAAAACCAA GAAAAGGCTT CTATCGCGGG CCACATGTTC

51 GACGTAGTCG TGATCGGAGG TGGCATTTCA GGACTATCTG CTGCCAAACT

101 CTTGACTGAA TATGGCGTTA GTGTTTTGGT TTTAGAAGCT CGGGACAGGG

151 TTGGAGGAAG AACATATACT ATAAGGAATG AGCATGTTGA TTACGTAGAT

201 GTTGGTGGAG CTTATGTGGG ACCAACCCAA AACAGAATCT TACGCTTGTC

251 TAAGGAGCTG GCATAGAGA CTTACAAAGT GAATGTCAGT GAGCGTCTCG

301 TTCAATATGT CAAGGGGAAA ACATATCCAT TTCGGGGCGC CTTTCCACCA

351 GTATGGAATC CCATTGCATA TTTGGATTAC AATAATCTGT GGAGGACAAT

401 AGATAACATG GGGAAGGAGA TTCCAACTGA TGCACCCTGG GAGGCTCAAC

451 ATGCTGACAA ATGGGACAAA ATGACCATGA AAGAGCTCAT TGACAAAATC

501 TGCTGGACAA AGACTGCTAG GCGGTTTGCT TATCTTTTTG TGAATATCAA

551 TGTGACCTCT GAGCCTCACG AAGTGTCTGC CCTGTGGTTC TTGTGGTATG

601 TGAAGCAGTG CGGGGGCACC ACTCGGATAT TCTCTGTCAC CAATGGTGGC

651 CAGGAACGGA AGTTTGTAGG TGGATCTGGT CAAGTGAGCG AACGGATAAT

701 GGACCTCCTC GGAGACCAAG TGAAGCTGAA CCATCCTGTC ACTCACGTTG

751 ACCAGTCAAG TGACAACATC ATCATAGAGA CGCTGAACCA TGAACATTAT

801 GAGTGCAAAT ACGTAATTAA TGCGATCCCT CCGACCTTGA CTGCCAAGAT

851 TCACTTCAGA CCAGAGCTTC CAGCAGAGAG AAACCAGTTA ATTCAGCGGC

901 TTCCAATGGG AGCTGTCATT AAGTGCATGA TGTATTACAA GGAGGCCTTC

951 TGGAAGAAGA AGGATTACTG TGGCTGCATG ATCATTGAAG ATGAAGATGC

1001 TCCAATTTCA ATAACCTTGG ATGACACCAA GCCAGATGGG TCACTGCCTG

1051 CCATCATGGG CTTCATTCTT GCCCGGAAAG CTGATCGACT TGCTAAGCTA

1101 CATAAGGAAA TAAGGAAGAA GAAAATCTGT GAGCTCTATG CCAAAGTGCT

1151 GGGATCCCAA GAAGCTTTAC ATCCAGTGCA TTATGAAGAG AAGAACTGGT

1201 GTGAGGAGCA GTACTCTGGG GGCTGCTACA CGGCCTACTT CCCTCCTGGG

1251 ATCATGACTC AATATGGAAG GGTGATTCGT CAACCCGTGG GCAGGATTTT

1301 CTTTGCGGGC ACAGAGACTG CCACAAAGTG GAGCGGCTAC ATGGAAGGGG

1351 CAGTTGAGGC TGGAGAACGA GCAGCTAGGG AGGTCTTAAA TGGTCTCGGG

1401 AAGGTGACCG AGAAAGATAT CTGGGTACAA GAACCTGAAT CAAAGGACGT

1451 TCCAGCGGTA GAAATCACCC ACACCTTCTG GGAAAGGAAC CTGCCCTCTG
```

```
1501 TTTCTGGCCT GCTGAAGATC ATTGGATTTT CCACATCAGT AACTGCCCTG

1551 GGGTTTGTGC TGTACAAATA CAAGCTCCTG CCACGGTCTT GA
```

Example 3—Production of Truncated NCS

The *T. flavum* NCS sequence, courtesy of Peter Facchini, was that of the N-terminal MO truncation. To construct the full-length gene, the first 30 nucleotides (coding for 10 amino acids) were included in the forward primer sequence used for cloning the gene. For other variants, such as the Δ19 N-terminal truncation, the forward primer was designed to amplify the gene beginning at the $20^{th}$ amino acid and including an additional start codon if the new starting amino acid was not a methionine. To compare expression levels qualitatively, we cloned each variant into a yeast expression vector containing a V5 epitope tag (pYES2-NT/A, Invitrogen), transformed the plasmids into the wild-type yeast strain using the standard LiAc/SSD/PEG method (Gietz, R D and Woods, RA. *Methods in Enzymology*, Vol. 350, pp. 87-96, 2002), and performed Western blot analysis on the total protein lysates. This showed that the *T. flavum* NCSΔ10 was the most highly expressed in yeast, consistent with *E. coli* studies.

Example 4—Measurement of Dopamine Production

Yeast strains were constructed to produce dopamine from tyrosine. A high-copy—TRP plasmid containing TYDC2 and CYP2D6 both between the TEF1 promoter and CYC1 terminator was tested in various yeast strains. The standard LiAc/SSD/PEG method was used to transform the plasmid(s) into yeast. The CYP2D6 activity is enhanced as evidenced by an increase in dopamine production when the background strain is W(R), which overexpresses CPR1 from the chromosome. An additional increase in dopamine accumulation is observed when cells are co-transformed with a second plasmid expressing additional copies of CPR1 from the tetO$_7$ promoter. Alterations to the growth media have also been shown to enhance the activity of P450s in yeast (Jiang, H and Morgan, J A. Biotechnology and Bioengineering, Vol. 85, No 2, pp. 130-7). Media containing 3.4 g/L yeast nitrogen base, 5 g/L casein hydrolysate, and 20 g/L glucose was shown to improve dopamine production over standard SC media. For measurement of tyramine and dopamine accumulation, the growth media can be analyzed directly by LC-MS. Intracellular concentrations can be estimated by preparation of cell extracts. Briefly, cells are pelleted at 6000 rpm for 5 min at 4° C. and the supernatant carefully removed. Using a pipette, pellets of the cell paste are dropped into liquid nitrogen and a mortar and pestle used to homogenize the cells. Metabolites are extracted with methanol and solids removed by centrifugation; the liquid is passed through a syringe filter to remove any remaining debris. Appropriate dilutions are made prior to LC-MS analysis using 20 μL injection volume. Samples were run on an Agilent ZORBAX SB-Aq 3×250 mm, 5 μm column with 0.1% acetic acid as solvent A and methanol as solvent B. A gradient elution is used to separate the metabolites of interest: 0-10 min at 100% A, 10-30 min 0-90% B, 30-35 min 90-0% B, followed by a 5 min equilibration at 100% A. Tyrosine, tyramine, dopamine, and L-dopa elute within the first 10 min so that an isocratic elution may be used if analyzing only these and/or similar metabolites. Following LC separation, metabolites are injected into an Agilent 6320 ion trap MSD for detection. Extracted ion chromatograms are used to identify peaks for selected ions and compared to available standards in terms of elution time and MS fingerprint.

Example 5—Measurement of Norcoclaurine Production

Norcoclaurine was produced using both in vivo and in vitro methods. For in vitro experiments, protocols were based on published work (Samanani, N, Liscombe, D K, and Facchini, P. *The Plant Journal*, Vol. 40, pp. 302-313). Both *E. coli* and yeast cells expressing NCS variants were lysed with B-PER or Y-PER (Pierce), respectively, and total protein extracts were used in the assay. In vitro reactions were analyzed by LC-MS. Samples were run on an Agilent ZORBAX SB-Aq 3×250 mm, 5 μm column with 0.1% acetic acid as solvent A and methanol as solvent B. A gradient elution is used to separate the metabolites of interest: 0-10 min at 100% A, 10-30 min 0-90% B, 30-35 min 90-0% B, followed by a 5 min equilibration at 100% A. Following LC separation, metabolites are injected into an Agilent 6320 ion trap MSD for detection. Norcoclaurine elutes at 21.2 min using this method. Without a commercially available standard, norcoclaurine is confirmed by its characteristic fragmentation pattern. With the ion trap set to perform MS/MS in the 272 ion, the major fragments of the parent ion of m/z=107 (benzyl) and m/z=161 (isoquinoline) were identified. For in vivo experiments, yeast cells expressing NCS were supplemented with dopamine (between 10 μM and 1 mM) and 4-HPA (custom synthesized from Biosynthesis, concentration undetermined). The above method was used to analyze the growth media directly to detect extracellular norcoclaurine accumulation.

Example 6—Production and Measurement of Reticuline and its Intermediates

For production of reticuline from the substrate norlaudanosoline (or laudanosoline), yeast cells were transformed with plasmids expressing various combinations of 6OMT, CNMT, and 4'OMT coding sequences using the standard LiAc/SSD/PEG method. Yeast cells were grown in SC media lacking uracil and tryptophan for plasmid maintenance. The growth media (SC–URA/–TRP) was supplemented with norlaudanosoline at concentrations between 1-5 mM from a 10 or 20 mM stock solution in water. Cells were grown in test tubes at 30° C. with shaking at 200 rpm; volumes ranged from 1-10 mL and time points were from 8 hrs up to 1 week following addition of substrate. Cells (or an aliquot of culture) were pelleted and the supernatant analyzed directly by LC-MS. Samples were run on an. Agilent ZORBAX SB-Aq 3×250 mm, 5 μm column with 0.1% acetic acid as solvent A and methanol as solvent B. A gradient elution is used to separate the metabolites of interest: 0-10 min at 100% A, 10-30 min 0-90% B, 30-35 min 90-0% B, followed by a 5 min equilibration at 100% A. Following LC separation, metabolites are injected into an Agilent 6320 ion trap MSD for detection. Reticuline elutes at 23.6 min with this method and the correct structure of this metabolite is confirmed by performing MS/MS on the 330 ion to produce the fragments m/z=136 and m/z=192. Based on the results from plasmid-based expression, the *P. somniferum* 6OMT and CNMT were selected with either the *P. somniferum* or *T. flavum* 4'OMT as the best enzyme combinations, and these sequences were integrated into the chromosome using homologous recombination. In addition, strains were constructed to test each enzyme individually, typically using a single high-copy plasmid with the TEF promoter driving expression of the coding sequence. For the 6OMT activity, the correct product, 6-O-methyl norlaudanosoline, was detected by LC-MS when norlaudanosoline was present in the growth media; in vitro assays based on published protocols and using yeast lysates were also used to confirm this activity (Ounaroon, A et. Al. *The Plant Journal*, Vol. 36, pp. 808-19). Yeast cells expressing the CNMT enzyme converted 6,7-dimethyl-1,2,3,4-tetrahydroisoquinoline present at 1 mM in the growth media to the correct N-methylated product in vivo. Yeast cells expressing the 4'OMT enzyme methylated the substrates norlaudanosoline and laudanosoline in vivo. The correct location of the methyl group addition to each substrate is confirmed by performing MS/MS on the selected ion in all cases.

Example 7—Production and Measurement of Downstream Metabolites of Reticuline

For production of metabolites beyond reticuline, yeast strains with chromosomal integrations of 6OMT, CNMT, and 4'OMT were used when possible. These host cells contained no selection markers, allowing for additional coding sequences to be introduced on plasmids. For production of scoulerine, a plasmid expressing BBE was transformed into reticuline-producing strain(s) using the standard LiAc/SSD/PEG method. For production of tetrahydrocolumbamine, plasmids expressing BBE and S9OMT were cotransformed. For production of canadine, plasmids expressing BBE, S9OMT, CYP719A, and ATR1 were cotransformed. Construction of a yeast strain to stably express ATR1 along with the reticuline-producing enzymes and transformed with BBE, S9OMT, and CYP719A plasmids showed an increase in CYP719A activity (compared to plasmid-based expression of ATR1) demonstrated by increased conversion of substrate to canadine. Metabolites were detected in the growth media when supplemented with 1 mM or greater norlaudanosoline or laudanosoline. Samples were run on an Agilent ZORBAX SB-Aq 3×250 mm, 5 μm column with 0.1% acetic acid as solvent A and methanol as solvent B. A gradient elution is used to separate the metabolites of interest: 0-10 min at 100% A, 10-30 min 0-90% B, 30-35 min 90-0% B, followed by a 5 min equilibration at 100% A. Following LC separation, metabolites are injected into an Agilent 6320 ion trap MSD for detection. For each metabolite in the pathway, MS/MS was performed and the spectra compared. Based on the patterns observed, it can be confirmed that the peak identified as canadine, for example, has the same molecular structure as its precursor, tetrahydrocolumbamine. For production of salutaridine, the yeast strain stably expressing 6OMT, CNMT, 4'OMT, and ATR1 was transformed with a plasmid expressing CYP2D6. When the growth media was supplemented with norlaudanosoline or laudanosoline, salutaridine was detected by LC-MS. The elution time of salutaridine is identical to that of scoulerine as expected although its fragmentation pattern, particularly the 165 ion, indicates that the structure is in the correct (R) conformation based on the reported fragmentation pattern of salutaridinol.

What is claimed is:

1. A method for the production of a benzylisoquinoline alkaloid product, the method comprising:

culturing an engineered non-plant cell under conditions suitable for protein production, the engineered non-plant cell comprising two heterologous coding sequences, wherein the two heterologous coding sequences encode a first and second enzyme, respectively, that are involved in a metabolic pathway that converts tyrosine into the benzylisoquinoline alkaloid product, wherein the first and second enzymes are operably connected along the metabolic pathway, wherein the benzylisoquinoline alkaloid product is selected from the group consisting of a norcoclaurine, coclaurine, N-methylcoclaurine, 3'-hydroxy-N-methylcoclaurine, reticuline, 6-O-methyl-norlaudanosoline, 6-O-methyl-laudanosoline, laudanine, scoulerine, tetrahydrocolumbamine, canadine, salutaridine, salutaridinol, salutaridinol-7-O-acetate, and thebaine, wherein the first enzyme involved in the metabolic pathway that produces the benzylisoquinoline alkaloid product catalyzes at least one reaction that is selected from the group consisting of: Tyrosine to L-DOPA; L-DOPA to Dopamine; 4-hydroxyphenylacetaldehyde and Dopamine to Norcoclaurine; Tyrosine to 4-hydroxyphenylpyruvate; and 4-hydroxyphenylpyruvate to 4-hydroxyphenylacetaldehyde, wherein the second enzyme involved in the metabolite pathway that produces the benzylisoquinoline alkaloid product catalyzes at least one reaction that is selected from the group consisting of: Norcoclaurine to Coclaurine; Coclaurine to N-Methylcoclaurine; N-Methylcoclaurine to 3'-hydroxy-N-methylcoclaurine; 3'-hydroxy-N-methylcoclaurine to Reticuline; Norlaudanosoline to 6-O-methyl-norlaudanosoline; 6-O-methyl-norlaudanosoline to 6-O-methyl-laudanosoline; 6-O-methyl-laudanosoline to Reticuline; Reticuline to Laudanine; Reticuline to Scoulerine; Scoulerine to Tetrahydrocolumbamine; Tetrahydrocolumbamine to Canadine; Reticuline to Salutaridine; Salutaridine to Salutaridinol; Salutaridinol to Salutaridinol-7-O-acetate; and Salutaridinol-7-O-acetate to Thebaine; and wherein an enzyme of the first and second enzymes catalyzes a reaction that produces the benzylisoquinoline alkaloid product.

2. The method of claim 1, wherein the engineered non-plant cell is selected from the group consisting of microbial cells, insect cells, mammalian cells, bacterial cells, and yeast cells.

3. The method of claim 1, wherein the engineered non-plant cell is cultured under in vitro conditions.

4. The method of claim 1, wherein the engineered non-plant cell is cultured under in vivo conditions.

5. The method of claim 1, wherein the engineered non-plant cell is cultured with a compound selected from the group consisting of tyrosine, tyramine, dopamine, 4-hydroxyphenylacetaldehyde, 4-hydroxyphenylpyruvate, norcoclaurine, coclaurine, N-methylcoclaurine, 3'-hydroxy-N-methylcoclaurine, reticuline, scoulerine, tetrahydrocolumbamine, laudanosoline, and norlaudanosoline.

6. The method of claim 1, further comprising:
recovering the benzylisoquinoline alkaloid product from the cell culture.

7. The method of claim 6, wherein the engineered non-plant cell is cultured with tyrosine, and wherein the recovered benzylisoquinoline alkaloid product is norcoclaurine.

8. The method of claim 6, wherein the engineered non-plant cell is cultured with tyrosine, and whecrein the recovered benzylisoquinoline alkaloid product is reticuline.

9. The method of claim 1, wherein recovering the benzylisoquinoline alkaloid product from the cell culture comprises separating the benzylisoquinoline alkaloid product from cellular material to provide a product stream having the benzylisoquinoline alkaloid product.

10. The method of claim 1, wherein the benzylisoquinoline alkaloid product is selected from the group consisting of norcoclaurine, coclaurine, N-methylcoclaurine, 3'-hydroxy-N-methylcoclaurine, reticuline, 6-O-methyl-laudanosoline, laudanine, scoulerine, tetrahydrocolumbamine, canadine, salutaridine, salutaridinol, salutaridinol-7-O-acetate, and thebaine.

11. A method for the production of a benzylisoquinoline alkaloid product, the method comprising:

culturing an engineered non-plant cell under conditions suitable for protein production, the engineered non-plant cell comprising two heterologous coding sequences, wherein the two heterologous coding sequences encode a first and second enzyme, respectively, that are involved in a metabolic pathway that converts tyrosine into the benzylisoquinoline alkaloid product, wherein the first and second enzymes are operably connected along the metabolic pathway, wherein the benzylisoquinoline alkaloid product is a protoberberine product, wherein the first enzyme involved in the metabolic pathway that produces the benzylisoquinoline alkaloid product catalyzes at least one reaction that is selected from the group consisting of: Tyrosine to L-DOPA; L-DOPA to Dopamine; 4-hydroxyphenylacetaldehyde and Dopamine to Norcoclaurine; Tyrosine to 4-hydroxyphenylpyruvate; and 4-hydroxyphenylpyruvate to 4-hydroxyphenylacetaldehyde, wherein the second enzyme involved in the metabolic pathway that produces the benylisoquinoline alkaloid product catalyzes at least one reaction that is selected from the group consistin, of: Norcoclaurine to Coclaurine; Coclaurine to N-Methylcoclaurine; N-Methylcoclaurine to 3'-hydroxy-N-mehylcoclaurine; 3'-hydroxy-N-methylcoclaurine to Reticuline; Norlaudanosoline to 6-O-methyl-norlaudanosoline; 6-O-methyl-norlaudanosoline to 6-O-methyl-laudanosoline; 6-O-methyl-laudanosoline to Reticuline; Reticuline to Scoulerine; Scoulerine to Tetrahydrocolumbamine; and Tetrahydrocolumbamine to Canadine, and wherein an enzyme of the first and second enzymes catalyzes a reaction that produces the protoberberine product.

12. The method of claim 11, wherein the protoberberine product is selected from the group consisting of scoulerine, tetrahydrocolumbamine, and canadine.

13. A method for the production of a benzylisoquinoline alkaloid product, the method comprising:

culturing an engineered non-plant cell under conditions suitable for protein production, the engineered non-plant cell comprising two heterologous coding sequences, wherein the two heterologous coding sequences encode a first and second enzyme, respectively, that are involved in a metabolic pathway that converts tyrosine into the benzylisoquinoline alkaloid product, wherein the first and second enzymes are operably connected along the metabolic pathway, wherein the benzylisoquinoline alkaloid product is a promorphinan product, wherein the first enzyme involved in the metabolic pathway that produces the benzylisoquinoline alkaloid product catalyzes at least one reaction that is selected from the group consisting of: Tyrosine to L-DOPA; L-DOPA to Dopamine; 4-hydroxyphenylacetaldehyde and Dopamine to Norcoclaurine; Tyrosine to 4-hydroxyphenylpyruvate; and 4-hydroxyphenylpyruvate to 4-hydroxyphenylacetaldehyde, wherein the second enzyme involved in the metabolic pathway that produces the benzylisoquinoline alkaloid product catalyzes at least one reaction that is selected from the group consisting of: Norcoclaurine to Coclaurine; Coclaurine to N-Methylcoclaurine; N-Methylcoclaurine to 3'-hydroxy-N-methylcoclaurine; 3'-hydroxy-N-methylcoclaurine to Reticuline; Norlaudanosoline to 6-O-methyl-norlaudanosoline; 6-O-methyl-norlaudanosoline to 6-O-methyl-laudanosoline; 6-O-methyl-laudanosoline to Reticuline; Reticuline to Salutaridine; Salutaridine to Salutaridinol; and Salutaridinol to Salutaridinol-7-O-acetate, and wherein an enzyme of the first and second enzymes catalyzes a reaction that produces the promorphinan product.

14. The method of claim 13, wherein the promorphinan product is selected from the group consisting of salutaridine, salutaridinol, and salutaridinol-7-O-acetate.

15. A method for the production of a benzylisoquinoline alkaloid product, the method comprising:

culturing an engineered non-plant cell under conditions suitable for protein production, the engineered non-plant cell comprising two hetcrologous coding sequences, wherein the two heterologous coding sequences encode a first and second enzyme, respectively, that are involved in a metabolic pathway that converts tyrosine into the benzylisoquinoline alkaloid product, wherein the first and second enzymes are operably connected along the metabolic pathway, wherein the benzylisoquinoline alkaloid product is a 1-benzylisoquinoline alkaloid product, wherein the first enzyme involved in the metabolic pathway that produces the benzylisoquinoline alkaloid product catalyzes at least one reaction that is selected from the group consisting of: Tyrosine to L-DOPA: L-DOPA to Dopamine; 4-hydroxyphenylacetaldehyde and Dopamine to Norcoclaurine; Tyrosine to 4-hydroxyphenylpyruvate; and 4-hydroxyphenylpyruvate to 4-hydroxyphenylacetaldehyde, wherein the second enzyme involved in the metabolic pathway that produces the benzylisoquinoline alkaloid product catalyzes at least one reaction that is selected from the group consisting of: Norcoclaurine to Coclaurine; Coclaurine to N-Methylcoclaurine; N-Methylcoclaurine to 3'-hydroxy-N-methylcoclaurine; 3'-hydroxy-N-methylcoclaurine to Reticuline; Norlaudanosoline to 6-O-methyl-norlaudanosoline; 6-O-methyl-norlaudanosoline to 6-O-methyl-laudanosoline; and 6-O-methyl-laudanosoline to Reticuline, and wherein an enzyme of the first and second enzymes catalyzes a reaction that produces the 1-benzylisoquinoline alkaloid product.

16. The method of claim 15, wherein the 1-benzylisoquinoline alkaloid product is selected from the group consisting of norcoclaurine, coclaurine, N-methylcoclaurine, 3'-hydroxy-N-methylcoclaurine, 6-O-methyl-norlaudanosoline, 6-O-methyl-laudanosoline, and reticuline.

17. The method of claim 1, further comprising incorporating the benzylisoquinoline alkaloid product into a compound having analgesic properties.

18. The method of claim 1, further comprising incorporating the benzylisoquinoline alkaloid product into a compound having antimalarial properties.

19. The method of claim 1, further comprising incorporating the benzylisoquinoline alkaloid product into a compound having cancer therapeutic properties.

* * * * *

SEQUENCE LISTING

```
<160> NUMBER OF SEQ ID NOS: 2

<210> SEQ ID NO 1
<211> LENGTH: 1508
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 1
gtcgacatgg cattggaagc actagtccct ttagctgtaa ttgtagcaat attcctgtta      60
ttggtagacc ttatgcatag aagacaaaga tgggctgcaa gatacccacc cggcccacta     120
cccttgccag gactaggtaa cctttacat gttgatttcc aaaatactcc gtactgtttt     180
gatcaattga ggagaagatt cggagatgtt ttcagtctgc agttggcatg gacaccagtc     240
gtcgttttaa atggtttggc tgcagtaaga gaagctttag ttacgcatgg cgaagatacg     300
gcggacaggc ctcctgtgcc cattacacag atattgggtt tcggacctag atctcagggt     360
gtattccttg cccgttacgg tcctgcgtgg agagaacaga gaaggttttc tgtatcaaca     420
cttaggaatt tgggtctagg caagaaatca ttggaacaat gggtgaccga ggaagccgct     480
tgtttgtgcg cagcctttgc taatcattct ggccgtcctt ttagacctaa tggattactt     540
gataaagcag tatctaatgt gattgcctcc ttaacatgtg tagacgtttt tgagtacgat     600
gacccaaggt ttttgagatt gttagatcta gcacaagagg gattaaagga agaaagtggt     660
ttcttgagag aggttttgaa tgctgttcca gtgctattac acattccagc cctagctgga     720
```

```
aaggtcttga gatttcaaaa ggctttctta acgcagcttg atgagttact tacagagcat    780
aggatgactt gggatcctgc tcaacccccg agagatctaa ccgaggcctt cctggctgaa    840
atggaaaaag caagggtaa tccggaaagt tccttcaatg atgaaaacct gagaattgtc     900
gtggcggact tgttctctgc cggaatggtg acaacgtcta ctactttggc ctggggactt    960
ctattaatga ttcttcatcc agacgtccag agaagagtgc aacaagaaat agatgatgtg   1020
ataggacaag ttagaaggcc agaaatgggt gaccaggcac atatgccata tacgactgct   1080
gtaatccatg aagtgcaacg ttttggggac attgtcccct gggaatgac ccacatgact    1140 tctcgtgata ttgaagtaca aggtttcaga ataccaaagg gaactacgct gattacgaat   1200
ctgtctagcg tgctaaaaga cgaagctgtc tgggagaagc catttaggtt tcatccagaa   1260
cacttcttag acgctcaggg tcatttcgta aagcctgaag cattccttcc gtttagtgcc   1320
ggacgtaggg cgtgtttggg tgaaccatta gctagaatgg aattattcct ttttttttaca  1380 tctttattgc agcacttttc attttctgtt ccgactggcc aacccagacc tagccatcat   1440 ggtgttttg ctttcctagt ttctccctct ccttatgaat tatgcgcggt tccccgttga    1500
gcggccgc                                                              1508
```

<210> SEQ ID NO 2
<211> LENGTH: 1592
<212> TYPE: DNA
<213> ORGANISM: Homo sapiens

<400> SEQUENCE: 2

```
aattaataat ggaaaaccaa gaaaaggctt ctatcgcggg ccacatgttc gacgtagtcg     60
tgatcggagg tggcatttca ggactatctg ctgccaaact cttgactgaa tatggcgtta   120
gtgttttggt tttagaagct cgggacaggg ttggaggaag aacatatact ataaggaatg    180
agcatgttga ttacgtagat gttggtggag cttatgtggg accaacccaa aacagaatct   240
tacgcttgtc taaggagctg gcatagaga cttacaaagt gaatgtcagt gagcgtctcg    300
ttcaatatgt caaggggaaa acatatccat ttcgggcgc ttttccacca gtatggaatc     360
ccattgcata tttggattac aataatctgt ggaggacaat agataacatg gggaaggaga   420
ttccaactga tgcaccctgg gaggctcaac atgctgacaa atgggacaaa atgaccatga   480
aagagctcat tgacaaaatc tgctggacaa agactgctag gcggttttgct tatcttttttg  540 tgaatatcaa tgtgacctct gagcctcacg aagtgtctgc cctgtggttc ttgtggtatg   600
tgaagcagtg cggggggcacc actcggatat tctctgtcac caatggtggc caggaacgga   660
agtttgtagg tggatctggt caagtgagcg aacggataat ggacctcctc ggagaccaag   720
tgaagctgaa ccatcctgtc actcacgttg accagtcaag tgacaacatc atcatagaga   780
cgctgaacca tgaacattat gagtgcaaat acgtaattaa tgcgatccct ccgaccttga    840
ctgccaagat tcacttcaga ccagagcttc cagcagagag aaaccagtta attcagcggc    900
ttccaatggg agctgtcatt aagtgcatga tgtattacaa ggaggccttc tggaagaaga   960
aggattactg tggctgcatg atcattgaag atgaagatgc tccaatttca ataaccttgg  1020
atgacaccaa gccagatggg tcactgcctg ccatcatggg cttcattctt gcccggaaag  1080
ctgatcgact tgctaagcta cataaggaaa taaggaagaa gaaaatctgt gagctctatg  1140
ccaaagtgct gggatcccaa gaagctttac atccagtgca ttatgaagag aagaactggt  1200
gtgaggagca gtactctggg ggctgctaca cggcctactt ccctcctggg atcatgactc  1260
aatatggaag ggtgattcgt caacccgtgg gcaggatttt ctttgcgggc acagagactg  1320
```

```
ccacaaagtg gagcggctac atggaagggg cagttgaggc tggagaacga gcagctaggg    1380
aggtcttaaa tggtctcggg aaggtgaccg agaaagatat ctgggtacaa gaacctgaat    1440
caaaggacgt tccagcggta gaaatcaccc acaccttctg ggaaaggaac ctgccctctg    1500
tttctggcct gctgaagatc attggatttt ccacatcagt aactgccctg gggtttgtgc    1560
tgtacaaata caagctcctg ccacggtctt ga                                  1592
```